US010428348B2

(12) United States Patent
Wei et al.

(10) Patent No.: US 10,428,348 B2
(45) Date of Patent: Oct. 1, 2019

(54) REPRODUCTION OF FEMALE STERILITY LINES AND ITS APPLICATION IN HYBRID SEED PRODUCTION

(71) Applicant: EXALT STATE HOLDINGS LIMITED, Tortola (VG)

(72) Inventors: Ning Wei, Beijing (CN); Haodong Chen, Beijing (CN); Zhongcheng Liang, Beijing (CN)

(73) Assignee: Exalt State Holdings Limited, Tortola (VG)

( * ) Notice: Subject to any disclaimer, the term of this patent is extended or adjusted under 35 U.S.C. 154(b) by 387 days.

(21) Appl. No.: 15/109,540

(22) PCT Filed: Dec. 29, 2014

(86) PCT No.: PCT/CN2014/095240
§ 371 (c)(1),
(2) Date: Jul. 1, 2016

(87) PCT Pub. No.: WO2015/101243
PCT Pub. Date: Jul. 9, 2015

(65) Prior Publication Data
US 2016/0326536 A1    Nov. 10, 2016

(30) Foreign Application Priority Data
Jan. 2, 2014  (CN) .......................... 2014 1 0001109

(51) Int. Cl.
C12N 15/82 (2006.01)
A01H 1/02 (2006.01)
C07K 14/415 (2006.01)

(52) U.S. Cl.
CPC ............. *C12N 15/829* (2013.01); *A01H 1/02* (2013.01); *C07K 14/415* (2013.01); *C12N 15/8287* (2013.01); *C12N 15/8289* (2013.01)

(58) Field of Classification Search
CPC . C12N 15/829; C12N 15/826; C12N 15/8261
See application file for complete search history.

(56) References Cited

U.S. PATENT DOCUMENTS

| | | | |
|---|---|---|---|
| 5,689,049 A | 11/1997 | Cigan et al. | |
| 5,962,769 A | 10/1999 | Albertsen et al. | |
| 2012/0331579 A1* | 12/2012 | Parish | C12N 15/113 800/278 |

FOREIGN PATENT DOCUMENTS

| | | |
|---|---|---|
| CN | 1206360 C | 6/2005 |
| CN | 101248183 A | 8/2008 |
| CN | 102731635 A | 10/2012 |
| CN | 103834684 A | 6/2014 |
| WO | 9325695 A1 | 12/1993 |
| WO | 96/017945 A1 | 6/1996 |

OTHER PUBLICATIONS

Dawson et al (1993, "Microspore and Pollen Development in Six Male-Sterile Mutants of *Arabidopsis thaliana*". Canadian Journal of Botany 71: 629-638).*
Dreni, L. et al. The Plant Journal, 2007; vol. 52, pp. 690-699.*
Mariani, et al.,Naturevol. 347; pp. 737; (1990).
Quaas, et al.,Eur. J. Biochem. vol. 173: pp. 617 (1988).
Hartley,J. Molec. Biol.; vol. 202: pp. 913 (1988).
Estruch, et al.,EMBO J. vol. 10: pp. 3125 (1991).
Spena, et al.,Theor. Appl. Genet.; vol. 84: pp. 520 (1992).
Slightom, et al.,J. Biol. Chem. vol. 261: pp. 108 (1986).
International Search Report of International Application No. PCT/CN2014/095240 dated Mar. 27, 2015.

* cited by examiner

*Primary Examiner* — Russell Kallis
(74) *Attorney, Agent, or Firm* — Michael X. Ye; Morris, Manning & Martin, LLP

(57) ABSTRACT

Provided in the present invention is a method for preparing hybrid rice, comprising the reproduction and maintenance of the female sterility line and the use thereof in preparing hybrid rice.

15 Claims, 10 Drawing Sheets
Specification includes a Sequence Listing.

Mutant          Wild-type

Mutant　　　　Wild-type

Mutant　　　　Wild-type

Mutant　　　　Wild-type

```
Wild-type    1   ATGGGGAGGGGCAGGATTGAGATCAAGAGGATCGAGAACACGACAAGCCGCCAGGTGACC
                 ||||||||||||||||||||||||||||||||||||||||||||||||||| |||||||
Mutant       1   ATGGGGAGGGGCAGGATTGAGATCAAGAGGATCGAGAACACGACAAGCCGCTAGGTGACC Wild-type   61   TTCTGCAAGCGCCGCAACGGGCTTCTCAAGAAGGCGTATGAGCTCTCCGTCCTCTGCGAT
                 ||||||||||||||||||||||||||||||||||||||||||||||||||||||||||||
Mutant      61   TTCTGCAAGCGCCGCAACGGGCTTCTCAAGAAGGCGTATGAGCTCTCCGTCCTCTGCGAT Wild-type  121   GCCGAGGTGGCTCTCATCGTCTTCTCCAGCCGTGGCCGCCTCTACGAGTACTCCAACAAC
                 ||||||||||||||||||||||||||||||||||||||||||||||||||||||||||||
Mutant     121   GCCGAGGTGGCTCTCATCGTCTTCTCCAGCCGTGGCCGCCTCTACGAGTACTCCAACAAC Wild-type  181   AACAATGTGAAGGCTACAATTGACAGGTACAAGAAGGCGCATGCTTGTGGCTCAACTTCT
                 ||||||||||||||||||||||||||||||||||||||||||||||||||||||||||||
Mutant     181   AACAATGTGAAGGCTACAATTGACAGGTACAAGAAGGCGCATGCTTGTGGCTCAACTTCT Wild-type  241   GGTGCACCTCTCATAGAGGTCAATGCTCAGCAATACTACCAGCAGGAGTCTGCCAAACTG
                 ||||||||||||||||||||||||||||||||||||||||||||||||||||||||||||
Mutant     241   GGTGCACCTCTCATAGAGGTCAATGCTCAGCAATACTACCAGCAGGAGTCTGCCAAACTG Wild-type  301   CGCCACCAGATTCAGATGCTGCAAAACACCAACAAGCACCTGGTTGGCGATAATGTGAGC
                 ||||||||||||||||||||||||||||||||||||||||||||||||||||||||||||
Mutant     301   CGCCACCAGATTCAGATGCTGCAAAACACCAACAAGCACCTGGTTGGCGATAATGTGAGC Wild-type  361   AACCTGTCACTGAAGGAGCTGAAGCAACTTGAAAGCCGCCTGGAGAAAGGCATTGCAAAG
                 ||||||||||||||||||||||||||||||||||||||||||||||||||||||||||||
Mutant     361   AACCTGTCACTGAAGGAGCTGAAGCAACTTGAAAGCCGCCTGGAGAAAGGCATTGCAAAG Wild-type  421   ATCAGAGCCAGGAAGAATGAACTGCTGGCTTCAGAGATCAATTACATGGCCAAAAGGGAG
                 ||||||||||||||||||||||||||||||||||||||||||||||||||||||||||||
Mutant     421   ATCAGAGCCAGGAAGAATGAACTGCTGGCTTCAGAGATCAATTACATGGCCAAAAGGGAG
```

Figure 6

```
Wild-type   481  ATTGAGCTTCAGAACGACAACATGGACCTCAGAACCAAGATTGCTGAGGAGGAGCAGCAG
                 ||||||||||||||||||||||||||||||||||||||||||||||||||||||||||||
Mutant      481  ATTGAGCTTCAGAACGACAACATGGACCTCAGAACCAAGATTGCTGAGGAGGAGCAGCAG Wild-type   541  CTGCAGCAGGTGACGGTGGCCCGGTCGGCCGCCATGGAGCTGCAGGCTGCGGCGGCGGCG
                 ||||||||||||||||||||||||||||||||||||||||||||||||||||||||||||
Mutant      541  CTGCAGCAGGTGACGGTGGCCCGGTCGGCCGCCATGGAGCTGCAGGCTGCGGCGGCGGCG Wild-type   601  CAGCAGCAGCAGCAGAATCCGTTCGCGGTGGCGGCGGCGCAGTTGGACATGAAGTGCTTC
                 ||||||||||||||||||||||||||||||||||||||||||||||||||||||||||||
Mutant      601  CAGCAGCAGCAGCAGAATCCGTTCGCGGTGGCGGCGGCGCAGTTGGACATGAAGTGCTTC Wild-type   661  TTCCCGTTGAACCTGTTCGAGGCGGCGGCGCAGGTGCAGGCCGTGGCGGCGCAGCGCCAG
                 ||||||||||||||||||||||||||||||||||||||||||||||||||||||||||||
Mutant      661  TTCCCGTTGAACCTGTTCGAGGCGGCGGCGCAGGTGCAGGCCGTGGCGGCGCAGCGCCAG Wild-type   721  CAGATCATCCCCACCGAGCTCAACCTCGGCTACCACCACCACCTCGCCATTCCCGGCGCC
                 ||||||||||||||||||||||||||||||||||||||||||||||||||||||||||||
Mutant      721  CAGATCATCCCCACCGAGCTCAACCTCGGCTACCACCACCACCTCGCCATTCCCGGCGCC Wild-type   781  ACCGCCGCCGACGCGCCGCCTCCTCACTTCTGA       (SEQ ID: 1)
                 |||||||||||||||||||||||||||||||||
Mutant      781  ACCGCCGCCGACGCGCCGCCTCCTCACTTCTGA       (SEQ ID: 5)
```

Figure 6 (cont'd)

```
Huang Huazhan    1    ATGGGGAGGGGCAGGATTGAGATCAAGAGGATCGAGAACACGACAAGCCGCCAGGTGACC    60
                      ||||||||||||||||||||||||||||||||||||||||||||||||||||||||||||
Nipponbare       1    ATGGGGAGGGGCAGGATTGAGATCAAGAGGATCGAGAACACGACAAGCCGCCAGGTGACC    60

Huang Huazhan    61   TTCTGCAAGCGCCGCAACGGGCTTCTCAAGAAGGCGTATGAGCTCTCCGTCCTCTGCGAT   120
                      |||||||||||||||||||||| |||||||||||||||||||||||||||||||||||||
Nipponbare       61   TTCTGCAAGCGCCGCAACGGACTTCTCAAGAAGGCGTATGAGCTCTCCGTCCTCTGCGAT   120

Huang Huazhan    121  GCCGAGGTGGCTCTCATCGTCTTCTCCAGCCGTGGCCGCCTCTACGAGTACTCCAACAAC   180
                      ||||||||||||||||||||||||||||||||||||||||||||||||||||||||||||
Nipponbare       121  GCCGAGGTGGCTCTCATCGTCTTCTCCAGCCGTGGCCGCCTCTACGAGTACTCCAACAAC   180

Huang Huazhan    181  AACAATGTGAAGGCTACAATTGACAGGTACAAGAAGGCGCATGCTTGTGGCTCAACTTCT   240
                      ||||||||||||||||||||||||||||||||||||||||||||||||||||||||||||
Nipponbare       181  AACAATGTGAAGGCTACAATTGACAGGTACAAGAAGGCGCATGCTTGTGGCTCAACTTCT   240
```

Figure 7

| | | | |
|---|---|---|---|
| Huang Huazhan | 241 | GGTGCACCTCTCATAGAGGTCAATGCTCAGCAATACTACCAGCAGGAGTCTGCCAAACTG | 300 |
| Nipponbare | 241 | GGTGCACCTCTCATAGAGGTCAATGCTCAGCAATACTACCAGCAGGAGTCTGCCAAACTG | 300 |
| Huang Huazhan | 301 | CGCCACCAGATTCAGATGCTGCAAAACACCAACAAGCACCTGGTTGGCGATAATGTGAGC | 360 |
| Nipponbare | 301 | CGCCACCAGATTCAGATGCTGCAAAACACCAACAAGCACCTGGTTGGCGATAATGTGAGC | 360 |
| Huang Huazhan | 361 | AACCTGTCACTGAAGGAGCTGAAGCAACTTGAAAGCCGCCTGGAGAAAGGCATTGCAAAG | 420 |
| Nipponbare | 361 | AACCTGTCACTGAAGGAGCTGAAGCAACTTGAAAGCCGCCTGGAGAAAGGCATTTCAAAG | 420 |
| Huang Huazhan | 421 | ATCAGAGCCAGGAAGAATGAACTGCTGGCTTCAGAGATCAATTACATGGCCAAAAGGGAG | 480 |
| Nipponbare | 421 | ATCAGAGCCAGGAAGAATGAACTGCTGGCTTCAGAGATCAATTACATGGCCAAAAGGGAG | 480 |
| Huang Huazhan | 481 | ATTGAGCTTCAGAACGACAACATGGACCTCAGAACCAAGATTGCTGAGGAGGAGCAGCAG | 540 |
| Nipponbare | 481 | ATTGAGCTTCAGAACGACAACATGGACCTCAGAACCAAGATTGCTGAGGAGGAGCAGCAG | 540 |
| Huang Huazhan | 541 | CTGCAGCAGGTGACGGTGGCCCGGTCGGCCGCCATGGAGCTGCAGGCTGCGGCGGCGGCG | 600 |
| Nipponbare | 541 | CTGCAGCAGGTGACGGTGGCCCGGTCGGCCGCCATGGAGCTGCAGGCTGCGGCGGCGGCG | 600 |
| Huang Huazhan | 601 | CAGCAGCAGCAGCAGAATCCGTTCGCGGTGGCGGCGGCGCAGTTGGACATGAAGTGCTTC | 660 |
| Nipponbare | 601 | CAGCAGCAGCAGCAGAATCCGTTCGCGGTGGCGGCGGCGCAGCTGGACATGAAGTGCTTC | 660 |
| Huang Huazhan | 661 | TTCCCGTTGAACCTGTTCGAGGCGGCGGCGCAGGTGCAGGCCGTGGCGGCGCAGCGCCAG | 720 |
| Nipponbare | 661 | TTCCCGTTGAACCTGTTCGAGGCGGCGGCGCAGGTGCAGGCCGTGGCGGCGCAGCGCCAG | 720 |
| Huang Huazhan | 721 | CAGATCATCCCCACCGAGCTCAACCTCGGCTACCACCACCACCTCGCCATTCCCGGCGCC | 780 |
| Nipponbare | 721 | CAGATCATCCCCACCGAGCTCAACCTCGGCTACCACCACCACCTTGCCATTCCCGGCGCC | 780 |
| Huang Huazhan | 781 | ACCGCCGCCGACGCGCCGCCTCCTCACTTCTGA | 813 (SEQ ID: 1) |
| Nipponbare | 781 | GCCGCCGCCGACGCGCCGCCTCCTCACTTCTGA | 813 (SEQ ID: 3) |

Figure 7 (cont'd)

```
Huang Huazhan1     MGRGRIEIKRIENTTSRQVTFCKRRNGLLKKAYELSVLCDAEVALIVFSSRGRLYEYSNN
                   ||||||||||||||||||||||||||||||||||||||||||||||||||||||||||||
Nipponbare   1     MGRGRIEIKRIENTTSRQVTFCKRRNGLLKKAYELSVLCDAEVALIVFSSRGRLYEYSNN Huang Huazhan61    NNVKATIDRYKKAHACGSTSGAPLIEVNAQQYYQQESAKLRHQIQMLQNTNKHLVGDNVS
                   ||||||||||||||||||||||||||||||||||||||||||||||||||||||||||||
Nipponbare   61    NNVKATIDRYKKAHACGSTSGAPLIEVNAQQYYQQESAKLRHQIQMLQNTNKHLVGDNVS Huang Huazhan121   NLSLKELKQLESRLEKGIAKIRARKNELLASEINYMAKREIELQNDNMDLRTKIAEEEQQ
                   |||||||||||||||||||| |||||||||||||||||||||||||||||||||||||||
Nipponbare   121   NLSLKELKQLESRLEKGISKIRARKNELLASEINYMAKREIELQNDNMDLRTKIAEEEQQ Huang Huazhan181   LQQVTVARSAAMELQAAAAAQQQQQNPFAVAAAQLDMKCFFPLNLFEAAAQVQAVAAQRQ
                   ||||||||||||||||||||||||||||||||||||||||||||||||||||||||||||
Nipponbare   181   LQQVTVARSAAMELQAAAAAQQQQQNPFAVAAAQLDMKCFFPLNLFEAAAQVQAVAAQRQ Huang Huazhan241   QIIPTELNLGYHHHLAIPGATAADAPPPHF
                   |||||||||||||||||||||| |||||||
Nipponbare   241   QIIPTELNLGYHHHLAIPGAAAADAPPPHF
```

Figure 8

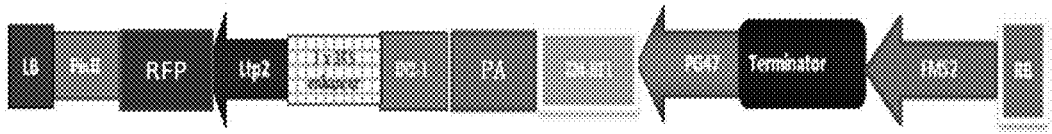

Figure 9

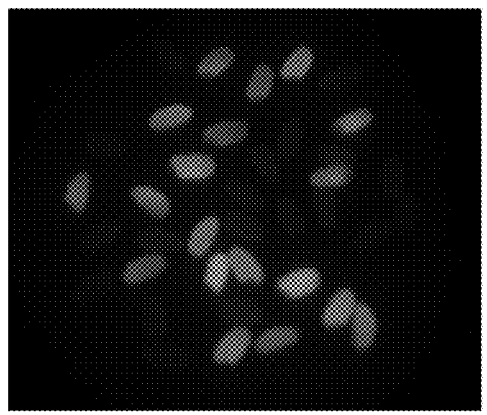

Figure 10

```
Wild-type   1   ATGGATCTCGTGTCGCCGTCCGAGCACCTGTGCTACGTGCGCTGCACCTACTGCAACACC   60
                ||||||||||||||||||||||||||||||||||||||||||||||||||||||||||||
Mutant      1   ATGGATCTCGTGTCGCCGTCCGAGCACCTGTGCTACGTGCGCTGCACCTACTGCAACACC   60

Wild-type  61   GTGCTCGCGCTGCAGGTTGGAGTCCCATGCAAGAGGCTGATGGACACCGTGACCGTGAAA  120
                |||||||||||||||||||||||| |||||||||||||||||||||||||||||||||||
Mutant     61   GTGCTCGCGCTGCAGGTTGGAGCCCCATGCAAGAGGCTGATGGACACCGTGACCGTGAAA  120

Wild-type 121   TGTGGCCACTGCAACAACCTCTCCTTCCTCAGCCCGCGGCCGCCGATGGTGCAGCCGCTC  180
                ||||||||||||||||||||||||||||||||||||||||||||||||||||||||||||
Mutant    121   TGTGGCCACTGCAACAACCTCTCCTTCCTCAGCCCGCGGCCGCCGATGGTGCAGCCGCTC  180

Wild-type 181   TCCCCAACTGATCACCCCTTGGGCCCGTTTCAGGGACCTTGCACTGACTGCAGGAGGAAC  240
                ||||||||||||||||||||||||||||||||||||||||||||||||||||||||||||
Mutant    181   TCCCCAACTGATCACCCCTTGGGCCCGTTTCAGGGACCTTGCACTGACTGCAGGAGGAAC  240

Wild-type 241   CAGCCGCTGCCGCTGGTCTCGCCGACATCAAATGAGGGTAGCCCAAGAGCACCCTTCGTT  300
                ||||||||||||||||||||||||||||||||||||||||||||||||||||||||||||
Mutant    241   CAGCCGCTGCCGCTGGTCTCGCCGACATCAAATGAGGGTAGCCCAAGAGCACCCTTCGTT  300

Wild-type 301   GTGAAGCCCCAGAGAAGAAACACCGCCTCCCATCTGCTTACAACCGCTTCATGAGGGAG   360
                ||||||||||||||||||||||||||||||||||||||||||||||||||||||||||||
Mutant    301   GTGAAGCCCCAGAGAAGAAACACCGCCTCCCATCTGCTTACAACCGCTTCATGAGGGAG   360

Wild-type 361   GAAATACAGCGTATCAAAGCTGCCAAGCCAGATATCCCTCACAGGGAGGCCTTCAGCATG  420
                ||||||||||||||||||||||||||||||||||||||||||||||||||||||||||||
Mutant    361   GAAATACAGCGTATCAAAGCTGCCAAGCCAGATATCCCTCACAGGGAGGCCTTCAGCATG  420

Wild-type 421   GCTGCCAAGAACTGGGCGAAGTGCGACCCCCGCTGCTCATCGACGGTTTCCACCTCCAAC  480
                ||||||||||||||||||||||||||||||||||||||||||||||||||||||||||||
Mutant    421   GCTGCCAAGAACTGGGCGAAGTGCGACCCCCGCTGCTCATCGACGGTTTCCACCTCCAAC  480

Wild-type 481   AGCAACCCCGAGCCCAGAGTAGTAGCTGCTCCCATTCCTCATCAGGAGAGGGCCAACGAG  540
                ||||||||||||||||||||||||||||||||||||||||||||||||||||||||||||
Mutant    481   AGCAACCCCGAGCCCAGAGTAGTAGCTGCTCCCATTCCTCATCAGGAGAGGGCCAACGAG  540

Wild-type 541   CAGGTGGTCGAGAGCTTCGACATCTTCAAGCAGATGGAGCGCAGCGGCTAG  591   (SEQ ID: 17)
                |||||||||||||||||||||||||||||||||||||||||||||||||||
Mutant    541   CAGGTGGTCGAGAGCTTCGACATCTTCAAGCAGATGGAGCGCAGCGGCTAG  591   (SEQ ID: 19)
```

Figure 13

```
Wild-type 1    MDLVSPSEHLCYVRCTYCNTVLALQVGVPCKRLMDTVTVKCGHCNNLSFLSPRPPMVQPL  60
               ||||||||||||||||||||||||||| ||||||||||||||||||||||||||||||||
Mutant    1    MDLVSPSEHLCYVRCTYCNTVLALQVGAPCKRLMDTVTVKCGHCNNLSFLSPRPPMVQPL  60

Wild-type 61   SPTDHPLGPFQGPCTDCRRNQPLPLVSPTSNEGSPRAPFVVKPPEKKHRLPSAYNRFMRE  120
               ||||||||||||||||||||||||||||||||||||||||||||||||||||||||||||
Mutant    61   SPTDHPLGPFQGPCTDCRRNQPLPLVSPTSNEGSPRAPFVVKPPEKKHRLPSAYNRFMRE  120

Wild-type 121  EIQRIKAAKPDIPHREAFSMAAKNWAKCDPRCSSTVSTSNSNPEPRVVAAPIPHQERANE  180
               ||||||||||||||||||||||||||||||||||||||||||||||||||||||||||||
Mutant    121  EIQRIKAAKPDIPHREAFSMAAKNWAKCDPRCSSTVSTSNSNPEPRVVAAPIPHQERANE  180

Wild-type 181  QVVESFDIFKQMERSG  196
               ||||||||||||||||
Mutant    181  QVVESFDIFKQMERSG  196
```

Figure 14

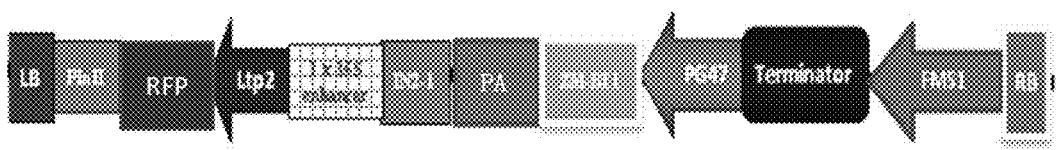

Figure 15

SEQUENCE LISTING

<160> NUMBER OF SEQ ID NOS: 23

<210> SEQ ID NO 1
<211> LENGTH: 813
<212> TYPE: DNA
<213> ORGANISM: Oryza sativa Indica

<400> SEQUENCE: 1

```
atggggaggg gcaggattga gatcaagagg atcgagaaca cgacaagccg ccaggtgacc      60
ttctgcaagc gccgcaacgg gcttctcaag aaggcgtatg agctctccgt cctctgcgat     120
gccgaggtgg ctctcatcgt cttctccagc cgtgccgcc tctacgagta ctccaacaac      180
aacaatgtga aggctacaat tgacaggtac aagaaggcgc atgcttgtgg ctcaacttct     240
ggtgcacctc tcatagaggt caatgctcag caatactacc agcaggagtc tgccaaactg     300
cgccaccaga ttcagatgct gcaaaacacc aacaagcacc tggttggcga taatgtgagc     360
aacctgtcac tgaaggagct gaagcaactt gaaagccgcc tggagaaagg cattgcaaag     420
atcagagcca ggaagaatga actgctggct tcagagatca attacatggc caaaagggag     480
attgagcttc agaacgacaa catggacctc agaaccaaga ttgctgagga ggagcagcag     540
ctgcagcagg tgacggtggc ccggtcggcc gccatggagc tgcaggctgc ggcggcggcg     600
cagcagcagc agcagaatcc gttcgcggtg gcggcggcgc agttggacat gaagtgcttc     660
ttcccgttga acctgttcga ggcggcggcg caggtgcagg ccgtggcggc gcagcgccag     720
cagatcatcc ccaccgagct caacctcggc taccaccacc acctcgccat tcccggcgcc     780
accgccgccg acgcgccgcc tcctcacttc tga                                  813
```

<210> SEQ ID NO 2
<211> LENGTH: 270
<212> TYPE: PRT
<213> ORGANISM: Oryza sativa Indica

<400> SEQUENCE: 2

```
Met Gly Arg Gly Arg Ile Glu Ile Lys Arg Ile Glu Asn Thr Thr Ser
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Arg Leu Tyr Glu Tyr Ser Asn Asn Asn Val Lys
    50                  55                  60

Ala Thr Ile Asp Arg Tyr Lys Lys Ala His Ala Cys Gly Ser Thr Ser
```

Gly Ala Pro Leu Ile Glu Val Asn Ala Gln Gln Tyr Tyr Gln Gln Glu
65                  70                  75                  80
                85                  90                  95

Ser Ala Lys Leu Arg His Gln Ile Gln Met Leu Gln Asn Thr Asn Lys
                100                 105                 110

His Leu Val Gly Asp Asn Val Ser Asn Leu Ser Leu Lys Glu Leu Lys
                115                 120                 125

Gln Leu Glu Ser Arg Leu Glu Lys Gly Ile Ala Lys Ile Arg Ala Arg
            130                 135                 140

Lys Asn Glu Leu Leu Ala Ser Glu Ile Asn Tyr Met Ala Lys Arg Glu
145                 150                 155                 160

Ile Glu Leu Gln Asn Asp Asn Met Asp Leu Arg Thr Lys Ile Ala Glu
                165                 170                 175

Glu Glu Gln Gln Leu Gln Gln Val Thr Val Ala Arg Ser Ala Ala Met
                180                 185                 190

Glu Leu Gln Ala Ala Ala Ala Gln Gln Gln Gln Asn Pro Phe
            195                 200                 205

Ala Val Ala Ala Ala Gln Leu Asp Met Lys Cys Phe Phe Pro Leu Asn
210                 215                 220

Leu Phe Glu Ala Ala Ala Gln Val Gln Ala Val Ala Ala Gln Arg Gln
225                 230                 235                 240

Gln Ile Ile Pro Thr Glu Leu Asn Leu Gly Tyr His His Leu Ala
                245                 250                 255

Ile Pro Gly Ala Thr Ala Ala Asp Ala Pro Pro His Phe
            260                 265                 270

<210> SEQ ID NO 3
<211> LENGTH: 813
<212> TYPE: DNA
<213> ORGANISM: Oryza sativa Japonica

<400> SEQUENCE: 3
atggggaggg gcaggattga gatcaagagg atcgagaaca cgacaagccg ccaggtgacc      60
ttctgcaagc gccgcaacgg acttctcaag aaggcgtatg agctctccgt cctctgcgat     120
gccgaggtgg ctctcatcgt cttctccagc cgtggccgcc tctacgagta ctccaacaac     180
aacaatgtga aggctacaat tgacaggtac aagaaggcgc atgcttgtgg ctcaacttct     240
ggtgcacctc tcatagaggt caatgctcag caatactacc agcaggagtc tgccaaactg     300
cgccaccaga ttcagatgct gcaaaacacc aacaagcacc tggttggcga taatgtgagc     360
aacctgtcac tgaaggagct gaagcaactt gaaagccgcc tggagaaagg catttcaaag     420
atcagagcca ggaagaatga actgctggct tcagagatca attacatggc caaaagggag     480
attgagcttc agaacgacaa catggacctc agaaccaaga ttgctgagga ggagcagcag     540
ctgcagcagg tgacggtggc ccggtcggcc gccatggagc tgcaggctgc ggcggcggcg     600
cagcagcagc agcagaatcc gttcgcggtg gcggcggcgc agctggacat gaagtgcttc     660
ttcccgttga acctgttcga ggcggcggcg caggtgcagg ccgtggcggc gcagcgccag     720
cagatcatcc ccaccgagct caacctcggc taccaccacc accttgccat tcccggcgcc     780
gccgccgccg acgcgccgcc tcctcacttc tga                                  813

<210> SEQ ID NO 4
<211> LENGTH: 270
<212> TYPE: PRT
<213> ORGANISM: Oryza sativa Japonica

<400> SEQUENCE: 4

```
Met Gly Arg Gly Arg Ile Glu Ile Lys Arg Ile Glu Asn Thr Thr Ser
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Arg Leu Tyr Glu Tyr Ser Asn Asn Asn Val Lys
    50                  55                  60

Ala Thr Ile Asp Arg Tyr Lys Lys Ala His Ala Cys Gly Ser Thr Ser
65                  70                  75                  80

Gly Ala Pro Leu Ile Glu Val Asn Ala Gln Gln Tyr Tyr Gln Gln Glu
                85                  90                  95

Ser Ala Lys Leu Arg His Gln Ile Gln Met Leu Gln Asn Thr Asn Lys
            100                 105                 110

His Leu Val Gly Asp Asn Val Ser Asn Leu Ser Leu Lys Glu Leu Lys
        115                 120                 125

Gln Leu Glu Ser Arg Leu Glu Lys Gly Ile Ser Lys Ile Arg Ala Arg
    130                 135                 140

Lys Asn Glu Leu Leu Ala Ser Glu Ile Asn Tyr Met Ala Lys Arg Glu
145                 150                 155                 160

Ile Glu Leu Gln Asn Asp Asn Met Asp Leu Arg Thr Lys Ile Ala Glu
                165                 170                 175

Glu Glu Gln Gln Leu Gln Gln Val Thr Val Ala Arg Ser Ala Ala Met
            180                 185                 190

Glu Leu Gln Ala Ala Ala Ala Gln Gln Gln Gln Asn Pro Phe
        195                 200                 205

Ala Val Ala Ala Ala Gln Leu Asp Met Lys Cys Phe Phe Pro Leu Asn
    210                 215                 220

Leu Phe Glu Ala Ala Ala Gln Val Gln Ala Val Ala Ala Gln Arg Gln
225                 230                 235                 240

Gln Ile Ile Pro Thr Glu Leu Asn Leu Gly Tyr His His His Leu Ala
                245                 250                 255

Ile Pro Gly Ala Ala Ala Ala Asp Ala Pro Pro His Phe
        260                 265                 270
```

<210> SEQ ID NO 5
<211> LENGTH: 813
<212> TYPE: DNA
<213> ORGANISM: Oryza sativa Indica

<400> SEQUENCE: 5

```
atggggaggg gcaggattga gatcaagagg atcgagaaca cgacaagccg ctaggtgacc      60
ttctgcaagc gccgcaacgg gcttctcaag aaggcgtatg agctctccgt cctctgcgat     120
gccgaggtgg ctctcatcgt cttctccagc cgtggccgcc tctacgagta ctccaacaac     180
aacaatgtga aggctacaat tgacaggtac aagaaggcgc atgcttgtgg ctcaacttct     240
ggtgcacctc tcatagaggt caatgctcag caatactacc agcaggagtc tgccaaactg     300
cgccaccaga ttcagatgct gcaaaacacc aacaagcacc tggttggcga taatgtgagc     360
aacctgtcac tgaaggagct gaagcaactt gaaagccgcc tggagaaagg cattgcaaag     420
atcagagcca ggaagaatga actgctggct tcagagatca attacatggc caaaagggag     480
attgagcttc agaacgacaa catggacctc agaaccaaga ttgctgagga ggagcagcag     540
```

```
ctgcagcagg tgacggtggc ccggtcggcc gccatggagc tgcaggctgc ggcggcggcg      600
cagcagcagc agcagaatcc gttcgcggtg gcggcggcgc agttggacat gaagtgcttc      660
ttcccgttga acctgttcga ggcggcggcg caggtgcagg ccgtggcggc gcagcgccag      720
cagatcatcc ccaccgagct caacctcggc taccaccacc acctcgccat tcccggcgcc      780
accgccgccg acgcgccgcc tcctcacttc tga                                   813
```

<210> SEQ ID NO 6
<211> LENGTH: 678
<212> TYPE: DNA
<213> ORGANISM: Artificial Sequence
<220> FEATURE:
<223> OTHER INFORMATION: Synthetic

<400> SEQUENCE: 6

```
atggcctcct ccgagaacgt gatcaccgag ttcatgcgct tcaaggtgcg catggagggc       60
accgtgaacg ccacgagtt cgagatcgag ggcgagggcg agggccgccc ctacgagggc       120
cacaacaccg tgaagctgaa ggtgaccaag ggcggccccc tgcccttcgc ctgggacatc      180
ctgtcccccc agttccagta cggctccaag gtgtacgtga agcaccccgc cgacatcccc      240
gactacaaga agctgtcctt ccccgagggc ttcaagtggg agcgcgtgat gaacttcgag      300
gacggcggcg tggccaccgt gacccaggac tcctccctgc aggacggctg cttcatctac      360
aaggtgaagt tcatcggcgt gaacttcccc tccgacggcc ccgtgatgca agaagaagacc     420 atgggctggg aggcctccac cgagcgcctg taccccgcg acggcgtgct gaagggcgag      480
acccacaagg ccctgaagct gaaggacggc ggccactacc tggtggagtt caagtccatc     540
tacatggcca agaagcccgt gcagctgccc ggctactact acgtggacgc caagctggac     600
atcacctccc acaacgagga ctacaccatc gtggagcagt acgagcgcac cgagggccgc     660
caccacctgt tcctgtag                                                    678
```

<210> SEQ ID NO 7
<211> LENGTH: 812
<212> TYPE: DNA
<213> ORGANISM: Hordeum vulgare

<400> SEQUENCE: 7

```
aaccgtctct tcgtgagaat aaccgtggcc taaaaataag ccgatgagga taaataaaat       60
gtggtggtac agtacttcaa gaggtttact catcaagagg atgcttttcc gatgagctct      120
agtagtacat cggacctcac atacctccat tgtggtgaaa tattttgtgc tcatttagtg      180
atgggtaaat tttgtttatg tcactctagg ttttgacatt tcagttttgc cactcttagg      240
ttttgacaaa taatttccat tccgcggcaa aagcaaaaca attttatttt acttttacca      300
ctcttagctt tcacaatgta tcacaaatgc cactctagaa attctgtttt tgccacagaa      360
tgtgaaaaaa aacactcact tatttgaagc caaggtgttc atggcatgga aatgtgacat      420
aaagtaacgt tcgtgtataa gaaaaaattg tactcctcgt aacaagagac ggaaacatca      480
tgagacaatc gcgtttggaa ggctttgcat cacctttgga tgatgcgcat gaatggagtc      540
gtctgcttgc tagccttcgc ctaccgccca ctgagtccgg cggcaacta ccatcggcga      600 acgacccagc tgacctctac cgaccggact tgaatgcgct accttcgtca gcgacgatgg      660
ccgcgtacgc tggcgacgtg cccccgcatg catggcggca catggcgagc tcagaccgtg      720
cgtggctggc tacaaatacg taccccgtga gtgccctagc tagaaactta cacctgcaac      780
```
tgcgagagcg agcgtgtgag tgtagccgag ta                                   812

<210> SEQ ID NO 8
<211> LENGTH: 331
<212> TYPE: DNA
<213> ORGANISM: Artificial Sequence
<220> FEATURE:
<223> OTHER INFORMATION: Synthetic

<400> SEQUENCE: 8
cgtcaacatg gtggagcacg acacgcttgt ctactccaaa aatatcaaag atacagtctc      60
agaagaccaa agggcaattg agacttttca acaaagggta atatccggaa acctcctcgg    120
attccattgc ccagctatct gtcactttat tgtgaagata gtggaaaagg aaggtggctc    180
ctacaaatgc catcattgcg ataaaggaaa ggccatcgtt gaagatgcct ctgccgacag    240
tggtcccaaa gatggacccc cacccacgag gagcatcgtg gaaaagaag acgttccaac     300 cacgtcttca aagcaagtgg attgatgtga t                                   331

<210> SEQ ID NO 9
<211> LENGTH: 331
<212> TYPE: DNA
<213> ORGANISM: Solanum tuberosum

<400> SEQUENCE: 9
cgtcaacatg gtggagcacg acacgcttgt ctactccaaa aatatcaaag atacagtctc      60
agaagaccaa agggcaattg agacttttca acaaagggta atatccggaa acctcctcgg    120
attccattgc ccagctatct gtcactttat tgtgaagata gtggaaaagg aaggtggctc    180
ctacaaatgc catcattgcg ataaaggaaa ggccatcgtt gaagatgcct ctgccgacag    240
tggtcccaaa gatggacccc cacccacgag gagcatcgtg gaaaagaag acgttccaac     300 cacgtcttca aagcaagtgg attgatgtga t                                   331

<210> SEQ ID NO 10
<211> LENGTH: 7493
<212> TYPE: DNA
<213> ORGANISM: Oryza sativa Indica

<400> SEQUENCE: 10
aatccagcca tatatatttg ttgcaattat cttttgtttt ggcagagtaa cctaaaggga      60
aattcgtacc ctatcaatca tattttttta gataaggcta aaaaaagcta ccactcactc    120
ttaagaatat gttaattgga agaaaaaaag agaagctacc attcattctc aagaatatgt    180
taattgaaga aaagagagc tatctacacc atccatcatg gtgggaccag attgtagcta     240
caaatgtatg gaaatacaa atgtatttgt agaaatagag aaaagttgc atatcaagta      300 cagtcatatt tcaaatagcc ctgtacaact gtgaaggaat ctcgactagt tgtctcttgg    360
tttgagggat atacctattt taggatgact gatatttcta gaaccacact ctaattcaaa    420
tctgctgatt tcatgtgtag agtacacact tctgatagat ttagcttctt aattgggcac    480
agctaactag ctagctctgc ccatttggtc tctccaattc tccatgagat aattaagtag    540
caatttataa gggattaaca aaatgcagca gcacacaaat actatatata tagccacatc    600
agtgtctgtc tgcataacag cataagatat agaagatgag ctgatcatca tatccatggc    660
agcaggccgg tgcagaatga agttcatgag gttcagaagt gaggaggcgg cgcgtcggcg    720
gcggtggcgc cgggaatggc gaggtggtgg tggtagccga ggttgagctc ggtgggatg    780 atctgctggc gctgcgccgc cacggcctgc acctgcgccg ccgcctcgaa caggttcaac    840

```
gggaagaagc acttcatgtc caactgcgcc gccgccaccg cgaacggatt ctgctgctgc    900
tgctgcgccg ccgccgcagc ctgcagctcc atggcggccg accgggccac cgtcacctgc    960
tgcagctgct gctcctcctc agcaatctgc aagtgtgcac atgatctctc atcaacgtat   1020
agtagagaca gatgtgtcgt tgatgtagag atatattgtt cttttcgtca agctttatag   1080
attaattagc tagctatttg ttcaaattaa tttaaacaaa tagctagcta attaatctct   1140
gatttgcaaa caagaaattg gaagttggtt ctgatttctt gcagtcacct gatatgtatt   1200
taccttggtt ctgaggtcca tgttgtcgtt ctgaagctca atctcctgaa atcatgacaa   1260
gaacattgca aatgagtaat gctaacaaga attatgcaat caggtaaaaa gaatagagga   1320
ttaagaaagg agtttgcaat cattgatcag tatgtacaat tgtatgtaag atgcaattct   1380
agtaacacac ataccctttt ggccatgtaa ttgatctctg aagccagcag ttcattctga   1440
gaaaaaatta aacaaataag gattaacagt taatttgtac attttttaagg ccacttagta   1500
agttaacatt gcatcagaaa ctgaagaatt gttcaaacaa agtaaatcaa ggtgatcata   1560
tatatctaac agcactgaga ttttgttcta aaggtgacac catgaggttg gtaattgaat   1620
gttcatgtga aaatggtatt ttatatatag ttgtttacct tcctggctct gatctttgca   1680
atgcctttct ccaggcggct ttcaagttgc ttcagctcct tcagtgacag gttgctcaca   1740
ttatcgccaa ccaggtgcct ttcacatagg aaaacaaacc aaacgaaaat aggtatttcc   1800
aggtcatcac attgattctg tcaagtaatc tcttttcaat attatcatcg atatatacac   1860
atgtgtttct tgaatggcag atataaaaat tgtgtattag tattaggcac ttacttgttg   1920
gtgttttgca gcatctgaat ctggtggcgc agtttggcag actcctgctg gtagtattgc   1980
ttcagacaag ataattaaca agacgatcga tcagatttaa ttacgtttat catgtagctc   2040
taattgatca gcaaaaaaaa aagtaacagt aaccttaatt gtagtgcaac agaatgactg   2100
cattcatgct tttacattga gtttatttt gtgaattttg tttgttctct tcagtcacta   2160
actttaaatt gcaagccact agccacaaaa gggtacactt acagtttcta agaaaagtat   2220
actcttaaac tcagagaaag acaaatatat ggagaacttc agtgcagaat tgcagactag   2280
gcattaggca atctccaagt ggttcacata ctacattaat tatgaattca atcttgtcgt   2340
aaagattgat gctgtatagc tataacacat gaatgtatat aagcacaaag atcaagccat   2400
accctgatga aactaacaaa ttaatataat gcagcagtca attacctacc acaaaaagta   2460
tataaaatac tttaaatgca aggcatctat atgctctcac tttatatgta tgaatatgcc   2520
ttggttttag aatagtcacc aaattaattt aactgaaact aaggcaaaat gaatagaaga   2580
aggtaattaa caaagcagca acatatatat gggttacctg agcattgacc tctatgagag   2640
gtgcaccaga agttgagcca caagcatgcg ccttcttgta cctgtcaatt gtagccttca   2700
cactgcagta tatatcccat cagtcgagtg gtactctctc aacactacaa cataaatact   2760
gataattgtg catgcatggt aatgtagtgt gttcatatat gccaacaaga gaagaaatgc   2820
aacacacatg actatacatg tcatgaatgc agaaataatg catgtgagga gcaagcgttt   2880
aattacttca gcataaaatt gtgcagaaga aaggtagcca ttggaatgca tgctgtctct   2940
agctgcaaga actgtgttga agcgaacaca agaacggaat gaaatgagta tacacgagct   3000
agagagaaag agagatggtc agatggatgg ccattggctt attaactgat gcacaacttt   3060
gcaccggaga agagcaaaca cagcgaatat gggaggacgt tgctgcagtt ctagcttgg   3120
tgcaagttct tctcatgcat gtccatggtg tctatatgtg tatcggtgta tggagaagca   3180
```

```
aggaaaagga aactcttgat agctagtttc tagggtgaac tatctactga acatacaaca    3240
ttgacaggag actgagcttc cttgctgtgc atgatatgat gtgtgttgtg tgaactgtgg    3300
agaataaaat atgataaaag atggcagtgg cttrgctagc tgctcaagta ctgatagcac    3360
tgatatatat tatgtaaagt ttgcatgcat gcatactcat gtacatgtac tcgagagaga    3420
ttgcaaatga atttgacatg tataaaaaca atgagacttt gcaaacttta ataattatt     3480 tgactgcatg catgaatgaa ttggaagggg attctaatgt atctttcaaa tagcctcccc    3540
ttaatatgtg tgtacatatc taattcacac atctcacttt gaaaatgatg agcaatagct    3600
aaggaatttt ccatggaggt taagagagta actttattta gatacaaaaa caatataatc    3660
atgcatgcat gacaaatcac catatatagt accatgcata tagtttgaaa taaatcttac    3720
aattttattt cgtaatctga gcagatgata actgaaaaaa gtaagcaagt cttgttacat    3780
gcacagatga aattaaagtc catgcataca tggttaattc tttccagcaa aatcaattta    3840
gcaagcagga tatataaatg gactttagta aagccttctg accataagac taagaaaatt    3900
agaacagaat aatccttttt caagtaacta acaggacaa cattttcagc attaatctta     3960
cagctagctg atgagcaaac atatacatct tgatgagttt ttatgataaa ctctaacatt    4020
tttcctaaat cattcacac cttgagttaa gtaattcaca tatcatctaa gaatgtgtat     4080
aatattaaac tcattctaaa atatttacca agagtcagtt ttaaccacaa ctaaactttt    4140
actcaataac aaactattag ccacaaataa agcaacacaa caagcacgct gagcatgaaa    4200
tgacacgaag ggaaacaaag caatcagcaa gatcagcaag ttagtttcaa gaactgagta    4260
caaaattaag ccaatatatt tacagcaagt acatacttgt tgttgttgga gtactcgtag    4320
aggcggccac ggctggagaa gacgatgaga gccacctcgg catcgcagag gacggagagc    4380
tcatacgcct tcttgagaag cccgttgcgg cgcttgcaga aggtcacctg gcggcttgtc    4440
gtgttctcga tcctcttgat ctcaatcctg cccctcccca tgtcttcttg ctctcaactg    4500
atcaacaaaa aaggagacca gagatcagat caaagaacag caaaaacatt gcatgagaag    4560
tttgatagat gcagaagaga gagtactgat gaaagatctg gtaatgatta agaacagca     4620 caaactctca gctgattaaa aaagagagag agaccggatt aaagaaacaa ctaaaacttg    4680
catgagaaat tgatagatgc agaaaagaga ctgatgaaag atctagtagt gatttacagt    4740
actacatcac acgctgatcg atctaagaaa ttaatgaatt caactatact gagagatctg    4800
agatcgtgat tcacatagta tgtgtataaa gtgatcgatc taacaaattc aagcatgttt    4860
tatacatgta aatccaaaag gaataagaaa ccagctatag ctaaagaggg gtaaaacaag    4920
agaaaaaaac tgaactttga agaaaaaga tgattttgc ttataaaaaa gaaagaaaaa      4980
gatgatgaaa gacttggcgg atatggatca aatttggaga ctgggacaat atctatccca    5040
tcatttgaca taagcaaagc tcaatcatcg cctatttaga agatatagag cctagatgca    5100
agtatagagt gatcgagtaa acaagatcta gcaaaagtag tctcaagaaa caaaactttc    5160
agatgtgcag agattgctcg aaataatgaa gggaagaagc gaaaagaaa gctcaaagaa     5220 ccagatgggt agatgaatca agaaggataa gatgcaagaa cagcacgtct ccacaaaaag    5280 gaaaaaaga accaaccaaa tctgaagaat catgtttaag aaagcatgga aaagctagca    5340
atttcgattt gcttaactaa ctatcttaac atatctagct aagaattgac caaagaaaac    5400
tcatcacaaa gtgagaagca agaggtcggc cgcaggaaac tagcttcttc cttttctcct    5460
gtctcctcac aagatcaaag atctgcctaa ggcaagaaga gaaatttcaa gaagaacga    5520 aaaaactgaa accttccaaa agaaaccagg atcactgggc cggaaagaat ccttgctaca    5580
```

```
taaatagaga aagaagctag gaagaatttc caatctgaac aaagaagcat caaactggaa      5640
gccaagcatc acagtttctc tttgcaagaa ctcgaagcac aggaaaaggg tttcttttcc      5700
tcaaagagag aacatacaaa cttgaatcta aactgcagct gaatcagtgc cttaacaaag      5760
aactctacac acacccagat aactaaaaca cattagcacg caaagagata tataacctag      5820
ctaaaattgg tcctgaagct gatctgatct ttctttctct accttcgttt cttggagtag      5880
gaaaggagag ctccagttgg tgggttttct gctgctgtgt gaggtgcaga ggattaatag      5940
gagaaggcaa agggaaagca ggaaagagag gaagaagggc tagctagcta gcttagctgc      6000
aaaggccact ggccttcttt gctatcttgc ttacccattt atagctattt agacatcttt      6060
gcatgtatat tctttaagca agaatttata acctctcttt ttttctatct tgtgtaattt      6120
gtgcctagaa acactgatct gcagagagga tatttagttg tttgtacttt gtaggcactg      6180
ctaaagtatg tttagagatt ggtcgatgtc cagaaggctg gagttataag caacctagca      6240
agttatgaaa aaaataagca actgatcatc ccttgttatg tgtttagtac atctgcagaa      6300
taactgaagt caacttgccg gttaattatc atatatgcat gcctagctag ttcttgcaaa      6360
tgttgtgtgc ttaattttgg aagaattagt tatataggtg ctaattctag aacttgatta      6420
gcatggacac attaagcagc cttttttgt tacacaagct ttcatattat ttccattatc       6480
acatgcacag ccacaactat atatatatat acacacacac acacttgctg ccctaattag      6540
atagtaagat gacttgctaa tcctgacata aatcgacagc tggttcaaat tggcatagta      6600
caaccttcca agtattttt gtctatcctt ggtttcaatt tccttggaga ggaaagatac       6660
atatgttgcc tatgtatgca tgcacagaaa accatacata cactgcatca cactgttgcg      6720
ttctttctaa cacacagtgt atatgcagct tctgagtaac ttgtattcaa ctcatatata      6780
tccatttatt atcttattaa aaagtacttt tttgttgcat gaatacatgc attgtctagt      6840
aatgtggcag ttcatttcct agccatgcat ctgcaatgca aaccaagtgg tagctactag      6900
atgctagttg gctagctagt tccaattgct tggcaattca catgcatata tatgaagaac      6960
acaccaacct ctcctagctt gcaaaagctc actgtaatat atagctagta cagcacagat      7020
aatatgaggc tgcagtgaca tggcaatata tgcaatccca aaccctatct ccattgctac      7080
ttgctatagc ctctcttgct atctctctct cactcccttg tgatgcaaat gcaatagcca      7140
gcagcattga ctgctagctg tgtgtactgc tgcatgcttg ccattcttgt tgctgttggt      7200
ggccagggag gagaacattt ctctccatgc ttgtttcagc tttcagattg aatgcatggt      7260
gccaaataaa ttaaatactt gaaagcctaa cctggaaggt tgcaaacttg caatcacgtt      7320
gtatatattt tgatgttagc atatatttag cactccaatt aactccatta gtttctttgt      7380 taatttttt atttcttt tttagagaag ggtattttg ttgttaatta gtttctagtt          7440
aatgtcccaa attattctgt actctgactg acaggatata ttggcgggta aac             7493
```

<210> SEQ ID NO 11
<211> LENGTH: 2971
<212> TYPE: DNA
<213> ORGANISM: Oryza sativa Indica

<400> SEQUENCE: 11

```
gtcagagtac agaataattt gggacattaa ctagaaacta attaacaaca aaatacccct        60
tctctaaaaa aagaaaataa aaaaattaac aaagaaaacta atggagttaa ttggagtgct      120
aaatatatgc taacatcaaa atatatacaa cgtgattgca agtttgcaac cttccaggtt       180
```

```
aggcttctcaa gtatttaatt tatttggcac catgcattca atctgaaagc tgaaacaagc     240
atggagagaa atgttctcct ccctggccac caacagcaac aagaatggca agcatgcagc     300
agtacacaca gctagcagtc aatgctgctg gctattgcat ttgcatcaca agggagtgag     360
agagagatag caagagaggc tatagcaagt agcaatggag atagggtttg ggattgcata     420
tattgccatg tcactgcagc ctcatattat ctgtgctgta ctagctatat attacagtga     480
gcttttgcaa gctaggagag gttggtgtgt tcttcatata tatgcatgtg aattgccaag     540
caattggaac tagctagcca actagcatct agtagctacc acttggtttg cattgcagat     600
gcatggctag gaaatgaact gccacattac tagacaatgc atgtattcat gcaacaaaaa     660 agtactttt aataagataa taaatggata tatatgagtt gaatacaagt tactcagaag     720
ctgcatatac actgtgtgtt agaaagaacg caacagtgtg atgcagtgta tgtatggttt     780
tctgtgcatg catacatagg caacatatgt atctttcctc tccaaggaaa ttgaaaccaa     840
ggatagacaa aaaatacttg gaaggttgta ctatgccaat ttgaaccagc tgtcgattta     900
tgtcaggatt agcaagtcat cttactatct aattagggca gcaagtgtgt gtgtgtgtat     960
atatatatat agttgtggct gtgcatgtga taatggaaat aatatgaaag cttgtgtaac    1020
aaaaaaaggc tgcttaatgt gtccatgcta atcaagttct agaattagca cctatataac    1080
taattcttcc aaaattaagc acacaacatt tgcaagaact agctaggcat gcatatatga    1140
taattaaccg gcaagttgac ttcagttatt ctgcagatgt actaaacaca taacaaggga    1200
tgatcagttg cttatttttt tcataacttg ctaggttgct tataactcca gccttctgga    1260
catcgaccaa tctctaaaca tactttagca gtgcctacaa agtacaaaca actaaatatc    1320
ctctctgcag atcagtgttt ctaggcacaa attacacaag atagaaaaaa agagaggtta    1380
taaattcttg cttaaagaat atacatgcaa agatgtctaa atagctataa atgggtaagc    1440
aagatagcaa agaaggccag tggcctttgc agctaagcta gctagctagc ccttcttcct    1500 ctcttcctg ctttccctt gccttctcct attaatcctc tgcacctcac acagcagcag    1560
aaaacccacc aactggagct ctcctttcct actccaagaa acgaaggtag agaaagaaag    1620
atcagatcag cttcaggacc aattttagct aggttatata tctcttttgcg tgctaatgtg    1680 ttttagttat ctgggtgtgt gtagagttct ttgttaaggc actgattcag ctgcagttta    1740
gattcaagtt tgtatgttct ctcttttgagg aaaagaaacc cttttcctgt gcttcgagtt    1800
cttgcaaaga gaaactgtga tgcttggctt ccagtttgat gcttctttgt tcagattgga    1860
aattcttcct agcttctttc tctatttatg tagcaaggat tctttccggc ccagtgatcc    1920
tggtttcttt tggaaggttt cagttttttc gttctttctt gaaatttctc ttcttgcctt    1980
aggcagatct ttgatcttgt gaggagacag gagaaaagga agaagctagt ttcctgcggc    2040
cgacctcttg cttctcactt tgtgatgagt tttctttggt caattcttag ctagatatgt    2100 taagatagt agttaagcaa atcgaaattg ctagcttttc catgctttct taaacatgat    2160
tcttcagatt tggttggttc ttttttttcct ttttgtggag acgtgctgtt cttgcatctt    2220
atccttcttg attcatctac ccatctggtt ctttgagctt tcttttttcgc ttcttcccctt    2280 cattatttcg agcaatctct gcacatctga aagttttgtt tcttgagact acttttgcta    2340
gatcttgttt actcgatcac tctatacttg catctaggct ctatatcttc taaataggcg    2400
atgattgagc tttgcttatg tcaaatgatg ggatagagat tgtcccagtc tccaaatttg    2460
atccatatcc gccaagtctt tcatcatctt ttcctttctt ttttataagc aaaaatcatc    2520 ttttctttc aaagttcagt ttttttctct tgttttaccc ctcttttagct atagctggtt    2580
```

```
tcttattcct tttggattta catgtataaa acatgcttga atttgttaga tcgatcactt    2640
tatacacata ctatgtgaat cacgatctca gatctctcag tatagttgaa ttcattaatt    2700
tcttagatcg atcagcgtgt gatgtagtac tgtaaatcac tactagatct ttcatcagtc    2760
tcttttctgc atctatcaat ttctcatgca agttttagtt gtttctttaa tccggtctct    2820
ctctcttttt taatcagctg agagtttgtg ctgttcttta atcattacca gatctttcat    2880
cagtactctc tcttctgcat ctatcaaact tctcatgcaa tgttttttgct gttctttgat   2940 ctgatctctg gtctcctttt ttgttgatca g                                    2971

<210> SEQ ID NO 12
<211> LENGTH: 440
<212> TYPE: DNA
<213> ORGANISM: Oryza sativa Indica

<400> SEQUENCE: 12
ctacacatga aatcagcaga tttgaattag agtgtggttc tagaaatatc agtcatccta      60
aaataggtat atccctcaaa ccaagagaca actagtcgag attccttcac agttgtacag     120
ggctatttga aatatgactg tacttgatat gcaactttttt ctctatttct acaaatacat    180
ttgtattttc catacatttg tagctacaat ctggtcccac catgatggat ggtgtagata    240
gctctctttt tcttcaatta acatattctt gagaatgaat ggtagcttct ctttttttct    300
tccaattaac atattcttaa gagtgagtgg tagctttttt tagccttatc taaaaaaata    360
tgattgatag ggtacgaatt tcccttttagg ttactctgcc aaaacaaaag ataattgcaa    420
caaatatata tggctggatt                                                 440

<210> SEQ ID NO 13
<211> LENGTH: 1488
<212> TYPE: DNA
<213> ORGANISM: Zea mays

<400> SEQUENCE: 13
atggcggcga caatggcagt gacgacgatg gtgacgagga gcaaggagag ctggtcgtca     60
ttgcaggtcc cggcggtggc attcccttgg aagccacgag gtggcaagac cggcggcctc    120
gagttccctc gccgggcgat gttcgccagc gtcggcctca acgtgtgccc gggcgtcccg    180
gcggggcgcg acccgcggga gcccgatccc aaggtcgtcc gggcggcctg cggcctggtc    240
caggcacaag tcctcttcca ggggtttaac tgggagtcgt gcaagcagca gggaggctgg    300
tacaacaggc tcaaggccca ggtcgacgac atcgccaagg ccggcgtcac gcacgtctgg    360
ctgcctccac cctcgcactc cgtctcgcca caaggctaca tgccaggccg cctatacgac    420
ctggacgcgt ccaagtacgg cacggcggcg gagctcaagt ccctgatagc ggcgttccac    480
ggcaggggcg tgcagtgcgt ggcggacatc gtcatcaacc accggtgcgc ggaaaagaag    540
gacgcgcgcg gcgtgtactg catcttcgag ggcgggactc ccgacgaccg cctgactgg    600 ggccccggga tgatctgcag cgacgacacg cagtactcgg acgggacggg gcaccgcgac    660
acgggcgagg ggttcgcggc ggcgcccgac atcgaccacc tcaacccgcg cgtgcagcgg    720
gagctctccg cctggctcaa ctggctcagg tccgacgccg tggggttcga cggctggcgc    780
ctcgacttcg ccaagggcta ctcgccggcc gtcgcagaa tgtacgtgga gagcacgggg    840
ccgccgagct tcgtcgtcgc ggagatatgg aactcgctga gctacagcgg ggacggcaag    900
ccggcgccca accaggacca gtgccggcag gagctgctgg actggacgcg ggccgtcggc    960
```

```
gggcccgcca tggcgttcga cttccccacc aagggcctgc tgcaggcggg cgtgcagggg    1020
gagctgtggc ggctgcgcga cagctccggc aacgcggccg gcctgatcgg gtgggcgccc    1080
gagaaggccg tcaccttcgt cgacaaccat gacaccgggt cgacgcagaa gctctggccg    1140
ttcccatccg acaaggtcat gcagggctac gcctacatcc tcacccatcc aggagtcccc    1200
tgcattttct acgaccacat gttcgactgg aacctgaagc aggagatatc cacgctgtct    1260
gccatcaggg cgcggaacgg catccgcgcc gggagcaagc tgcggatcct cgtgcggac     1320
gcggacgcgt acgtggccgt cgtcgacgag aaggtcatgg tgaagatcgg gacaaggtac    1380
ggcgtgagca cgtggtcccc gtcggatttc caccggcgg cgcacggcaa ggactactgc     1440
gtctgggaga agcgagcct ccgcgtcccg gcggggcgcc acctctag                  1488

<210> SEQ ID NO 14
<211> LENGTH: 2737
<212> TYPE: DNA
<213> ORGANISM: Zea mays

<400> SEQUENCE: 14
tgcaccggac actgtctggt ggcataccag acagtccggt gtgccagatc agggcaccct     60
tcggttcctt tgctcctttg cttttgaacc ctaactttga tcgtttattg gtttgtgttg    120
aacctttatg cacctgtgga atatataatc tagaacaaac tagttagtcc aatcatttgt    180
gttgggcatt caaccaccaa aattatttat aggaaaaggt taaaccttat ttcccttttca   240
atctccccct ttttggtgat tgatgccaac acaaaccaaa gaaatatat aagtgcagaa     300
ttgaactagt ttgcataagg taagtgcata ggttacttag aattaaatca atttatactt    360
ttacttgata tgcatggttg cttttctttta ttttaacatt ttggaccaca tttgcaccac   420
ttgttttgtt ttttgcaaat cttttttggaa attcttttttc aaagtctttt gcaaatagtc   480
aaaggtatat gaataagatt gtaagaagca ttttcaagat ttgaaatttc tccccctgtt    540
tcaaatgctt ttcctttgac taaacaaaac tcccctgaa taaaattctc ctcttagctt     600
tcaagagggt tttaaataga tatcaattgg aaatatattt agatgctaat tttgaaaata    660
taccaattga aaatcaacat accaatttga aattaaacat accaatttaa aaaatttcaa    720
aaagtggtgg tgcggtcctt ttgctttggg cttaatattt ctcccccttt ggcattaatc    780
gccaaaaacg gagactttgt gagccattta tactttctcc ccattggtaa atgaaatatg    840
agtgaaagat tataccaaat ttggacagtg atgcggagtg acggcgaagg ataaacgata    900
ccgttagagt gggagtggaag ccttgtcttc gccgaagact ccatttccct ttcaatctac    960
gacttagcat agaaatacac ttgaaaacac attagtcgta gccacgaaag agatatgatc   1020
aaaggtatac aaatgagcta tgtgtgtaat gtttcaatca aagtttcgag aatcaagaat   1080
atttagctca ttcctaagtt tgctaaaggt tttatcatct aatggtttgg taaagatatc   1140
gactaattgt tctttggtgc taacataagc aatctcgata tcacccccttt gttggtgatc   1200
cctcaaaaag tgataccgaa tgtctatgtg cttagtgcgg ctgtgttcaa cgggattatc   1260
cgccatgcag atagcactct cattgtcaca taggagaggg actttgctca atttgtagcc   1320
atagtcccta aggttttgcc tcatccaaag taattgcaca caacaatgtc ctgcggcaat   1380
atacttggct tcggcggtag aaaagagctat tgagttttgt ttctttgaag tccaagacac   1440
cagggatctc cctagaaact gacaagtccc tgatgtgctc ttcctatcaa ttttacaccc   1500
tgcccaatcg gcatctgaat atcctattaa atcaaaggtg gatcccttgg ggtaccaaag   1560
accaaattta ggagtgtaaa ctaaatatct catgattctt ttcacggccc taaggtgaac   1620
```

```
ttccttagga tcggcttgga atcttgcaca catgcatata gaaagcatac tatctggtcg    1680
agatgcacat aaatagagta aagatcctat catcgaccgg tataccttt ggtctacgga    1740 tttacctccc gtgtcgaggt cgagatgccc attagttccc atgggtgtcc tgatgggctt    1800
ggcatccttc attccaaact tgttgagtat gtcttgaatg tactttgttt ggctgatgaa    1860
ggtgccatct tggagttgct tgacttgaaa tcctagaaaa tatttcaact tccccatcat    1920
agacatctcg aatttcggaa tcatgatcct actaaactct tcacaagtag atttgttagt    1980
agacccaaat ataatatcat caacataaat ttggcataca aacaaaactt tgaaatggt    2040 tttagtaaag agagtaggat cggctttact gactctgaag ccattagtga taagaaaatc    2100
tcttaggcat tcataccatg ctgttggggc ttgcttgagc ccataaagcg cctttgagag    2160
tttataaaca tggttagggt actcactatc ttcaaagccg agaggttgct caacatagac    2220
ctattcaccc catttgatca ctttttggt ccttcaggat ctaatagtta tgtataattt    2280
agagtctctt gtttaatggc cagatatttc taattaatct aagaatttat gatatttttt    2340 aatttttat catgtctgat gagaattaac ataaaggctc aattgggtcc tgaattaata    2400
atagagtgaa aattaatcca gaggctctat tagaaccttc aattagtaat accaagatat    2460
atataagata gtagagtata gtttaaatgt tggcattgtt cattctttct tttgttattt    2520
aatttatgct ttccacggtg gttagtggtt acttctgaag ggtccaaata atgcatgaag    2580
agtttgagga caagaagtct gccctaaaaa tagcgatgca aaggcatggt gtccaagcca    2640
tacatatagc gcactaattt tatcagcaga acaatggtat ttataggtcc tagtgcccag    2700
gcaacaagag acacgaataa agcatcgatc acgacac                             2737

<210> SEQ ID NO 15
<211> LENGTH: 225
<212> TYPE: DNA
<213> ORGANISM: Zea mays

<400> SEQUENCE: 15
atggcggcga caatggcagt gacgacgatg gtgacgagga gcaaggagag ctggtcgtca     60
ttgcaggtcc cggcggtggc attcccttgg aagccacgag gtggcaagac cggcggcctc    120
gagttccctc gccgggcgat gttcgccagc gtcggcctca acgtgtgccc gggcgtcccg    180
gcggggcgcg acccgcggga gcccgatccc aaggtcgtcc gggcg                    225

<210> SEQ ID NO 16
<211> LENGTH: 348
<212> TYPE: DNA
<213> ORGANISM: Zea mays

<400> SEQUENCE: 16
gatctgacaa agcagcatta gtccgttgat cggtggaaga ccactcgtca gtgttgagtt     60
gaatgtttga tcaataaaat acggcaatgc tgtaagggtt gttttttatg ccattgataa    120
tacactgtac tgttcagttg ttgaactcta tttcttagcc atgccaagtg cttttcttat    180
tttgaataac attacagcaa aaagttgaaa gacaaaaaaa aaaaccccg aacagagtgc    240 tttgggtccc aagctacttt agactgtgtt cggcgttccc cctaaatttc tccccctata    300
tctcactcac ttgtcacatc agcgttctct ttcccctata tctccacg                 348

<210> SEQ ID NO 17
<211> LENGTH: 591
<212> TYPE: DNA
```

<213> ORGANISM: Oryza sativa Indica

<400> SEQUENCE: 17

```
atggatctcg tgtcgccgtc cgagcacctg tgctacgtgc gctgcaccta ctgcaacacc      60
gtgctcgcgc tgcaggttgg agtcccatgc aagaggctga tggacaccgt gaccgtgaaa     120
tgtggccact gcaacaacct ctccttcctc agcccgcggc cgccgatggt gcagccgctc     180
tccccaactg atcaccccct tgggccgttt cagggaccct gcactgactg caggaggaac     240
cagccgctgc cgctggtctc gccgacatca aatgagggta gcccaagagc acccttcgtt     300
gtgaagcccc cagagaagaa acaccgcctc ccatctgctt acaaccgctt catgagggag     360
gaaatacagc gtatcaaagc tgccaagcca gatatccctc acagggaggc cttcagcatg     420
gctgccaaga ctgggcgaa gtgcgacccc cgctgctcat cgacggtttc cacctccaac     480
agcaaccccg agcccagagt agtagctgct cccattcctc atcaggagag ggccaacgag     540
caggtggtcg agagcttcga catcttcaag cagatggagc gcagcggcta g              591
```

<210> SEQ ID NO 18
<211> LENGTH: 196
<212> TYPE: PRT
<213> ORGANISM: Oryza sativa Indica

<400> SEQUENCE: 18

```
Met Asp Leu Val Ser Pro Ser Glu His Leu Cys Tyr Val Arg Cys Thr
1               5                   10                  15

Tyr Cys Asn Thr Val Leu Ala Leu Gln Val Gly Val Pro Cys Lys Arg
            20                  25                  30

Leu Met Asp Thr Val Thr Val Lys Cys Gly His Cys Asn Asn Leu Ser
        35                  40                  45

Phe Leu Ser Pro Arg Pro Pro Met Val Gln Pro Leu Ser Pro Thr Asp
    50                  55                  60

His Pro Leu Gly Pro Phe Gln Gly Pro Cys Thr Asp Cys Arg Arg Asn
65                  70                  75                  80

Gln Pro Leu Pro Leu Val Ser Pro Thr Ser Asn Glu Gly Ser Pro Arg
                85                  90                  95

Ala Pro Phe Val Val Lys Pro Pro Glu Lys Lys His Arg Leu Pro Ser
            100                 105                 110

Ala Tyr Asn Arg Phe Met Arg Glu Glu Ile Gln Arg Ile Lys Ala Ala
        115                 120                 125

Lys Pro Asp Ile Pro His Arg Glu Ala Phe Ser Met Ala Ala Lys Asn
    130                 135                 140

Trp Ala Lys Cys Asp Pro Arg Cys Ser Ser Thr Val Ser Thr Ser Asn
145                 150                 155                 160

Ser Asn Pro Glu Pro Arg Val Val Ala Ala Pro Ile Pro His Gln Glu
                165                 170                 175

Arg Ala Asn Glu Gln Val Val Glu Ser Phe Asp Ile Phe Lys Gln Met
            180                 185                 190

Glu Arg Ser Gly
        195
```

<210> SEQ ID NO 19
<211> LENGTH: 591
<212> TYPE: DNA
<213> ORGANISM: Oryza sativa Indica

<400> SEQUENCE: 19

| | |
|---|---|
| atggatctcg tgtcgccgtc cgagcacctg tgctacgtgc gctgcaccta ctgcaacacc | 60 |
| gtgctcgcgc tgcaggttgg agccccatgc aagaggctga tggacaccgt gaccgtgaaa | 120 |
| tgtggccact gcaacaacct ctccttcctc agcccgcggc cgccgatggt gcagccgctc | 180 |
| tccccaactg atcacccctt gggccgtttt cagggaccct gcactgactg caggaggaac | 240 |
| cagccgctgc cgctggtctc gccgacatca atgagggta gcccaagagc acccttcgtt | 300 |
| gtgaagcccc cagagaagaa acaccgcctc ccatctgctt acaaccgctt catgagggag | 360 |
| gaaatacagc gtatcaaagc tgccaagcca gatatccctc acagggaggc cttcagcatg | 420 |
| gctgccaaga ctgggcgaa gtgcgacccc cgctgctcat cgacggtttc cacctccaac | 480 |
| agcaaccccg agcccagagt agtagctgct cccattcctc atcaggagag ggccaacgag | 540 |
| caggtggtcg agagcttcga catcttcaag cagatggagc gcagcggcta g | 591 |

<210> SEQ ID NO 20
<211> LENGTH: 5426
<212> TYPE: DNA
<213> ORGANISM: Oryza sativa Indica

<400> SEQUENCE: 20

| | |
|---|---|
| cagtaaaagg cagcccatca taagctttca ttaattagcg gtacgtgtac tttttcactg | 60 |
| aagctaggag catgcctaaa cgtacctgca actctcatgt gaaaaactca cctactaaca | 120 |
| taatcgatta gtcacgagtg cataatgaac acatatagct agtgtcgatc ggccgtatca | 180 |
| tcaaagtatg ttatctggac ctacaataat cgaccagctt atcgattgaa agacaaaaag | 240 |
| gttgtacgta tagtttgcta ggtagcattg gtacgttgta ctccttatat attgtcaaat | 300 |
| gacttgatat aaagtatgta gtagcacata taaggcacg caacagttgc tactttccca | 360 |
| gcttgctgtc tgagtgatct ctgaactgtt cttttgttct caatgaacaa taaacataaa | 420 |
| agcgatgtta tatcatttt ggccctgaat gttagtgcag atattaacat atatatagat | 480 |
| actcgtgcat catggatgca tcaagataaa cctaaccgca aaacatttg catgcatgta | 540 |
| tgcacacata tccttaaaaa atatccgtgc ttgcttaatt tgattattgt ttcattattt | 600 |
| gcatatataa gaagccaaat gaagatcagt tagctccttt tttacataaa tatggttgga | 660 |
| ccagcagctc taaattctaa tccaatacta gaaagtgaag ttttattcgc aactgaaaac | 720 |
| accagtggcg aaaacaacag ccaaacaaca tgttaataat tagatcgatc ccctcccctca | 780 |
| cacacacccc ccgtggcgtc gccatcggag cttctgttca tgtgtctccg atctgcagca | 840 |
| gagctttgcc ttttaatt gtccggagat gcatgcatcg atcgatccaa acagctcgat | 900 |
| cgatcgatcg atctcgaccg cacatcggtc catcgatcga tcgatcgacc gaacatagga | 960 |
| tcatgttggg tttaatgtt tctaattcgt acgaggacac aatatacatc gatcgatccg | 1020 |
| tggcgtacgt gtgcgtcgtc gtacaagaag cagtcccatg cactaagctt ctcgtatgta | 1080 |
| cagtgctcat gagtcgtaca tacatcctct tctaatgcta agtcacacac atgtacacac | 1140 |
| gctgatcatg ctcgatctag tcaagaccaa acaagctggc agcaaccaat gatcgatcta | 1200 |
| gtgaaatgtc tcgatcgatc cgccatcgac ttccttgcag tttccaacag ggtaattact | 1260 |
| taacacagac gataattctg ttaattagtt accatgtatg ggtatgcgta tcaattaatt | 1320 |
| tatgtagtaa atgtccacga tcagcttttc caaatactct taactactat aatttatctg | 1380 |
| aatttacttc ttctaaaaca ctcctaaaaa agattggaag tacactagtc acgcataatc | 1440 |
| aatagaaata tttttattat taatttact aatgcgattt ttatttgaaa aatcatatac | 1500 |
| ttattttca tatatttata tttaaagaat tatctataag aaaattatta ttattgaaat | 1560 |

-continued

```
cgagccagcc caactggtgt tatattaaga agagaaaata tgtatacaca aggtgctgtc   1620
aactactccc tccattttat attgtagtcg ttttactctt tttttcttgt caaactttat   1680
caaatttgac caattttata gaaaaaatta gcaacatata aaatatcaaa ttagtttcat   1740
taaatcgaac attaaatata ttttaataat atgtttgttt tatgttgaaa atactactat   1800 attttctat aaatttaatc aaacttgaaa aagtttgact aagaaaaaag tcaaacgact    1860
tataatatga aatggaggga gtaattacaa aataaaactg agaaacctac tacattcctc   1920
aacaactcaa atgccagtta aggaagatat tctctaaaga tttcacacca cacaagctcc   1980
aaagtttcat ttccgatcct ccatagaaaa aagaaactcc tagatatttc aattttcaaa   2040
aaacatttca aaatctata aactgcagag attattttag gtgctctgag aactaacacc    2100
tagatattta attaggaacc tggctagcta ggggtatatg tcaagcagta ccggtactat   2160
cttccgagtc agagagagag ggagcaattg gaccattcac aatttgaggg cacagtacaa   2220
ggcacaactg gatgggatgt agtactactg tggcttcgcc accggatcgg atggacacca   2280
ctctagctag ttactgtaag catatgctat agctagctat aggagcaaac atatactgtt   2340
cccatagcct cgagatgcat atgatattac gatgtgtaga gtacatgtac acatatggag   2400
agagagagag agagagagag atagaagaga cctgtcagat cactatgctg agttatacat   2460
atatacgtac atgaaaaagt ctttctacac gttataagag aatatcccgt gcttcttaca   2520
caccatctct atatttttc aaaagagaa attttaccgt tcttgagaaa atatcaaggt     2580
actaaacgtt aacgttagta aatatggttc actaggtatc tttttaatga tggtaaaatt   2640 accatttaa aaaagatgtt tctcttttc gtttcgacaa gatagagcgg tgtatgttga     2700
tatatccatc catccaacca tggatctcat ctcgctatct atcttagctt tgcttgcaac   2760
atttgcctcg aaagaaagaa ataaagaaaa ggaaaaataa aaacttttct ggtgctcgct   2820
ctcccgatca ctgtggttgg tctcgtgcgt acggggtcca tgtgtgcgtg ggaccccctc   2880
gccattattg caacaataga aaccctaccc catccttcct ctctcccgct gtgcccaact   2940
ctcccccccc cctctctttc tctctcctcc ttccgtctt cttcctccgg cctcttctcc    3000
tcttattgcc cttgattccc ccgcaccacc gctcacactt gctcctcctc ctcctcctcc   3060
tccgcctcag tgctagggct agcggatccg cctcagtgct agggctagct tgcttgtcgc   3120
cgtcgccgcc gtcgtcgccg ccgcaatgga tctcgtgtcg ccgtccgagc acctgtgcta   3180
cgtgcgctgc acctactgca acaccgtgct cgcgctgcag gttggagtcc catgcaagag   3240
gctgatggaa ccgtgaccg tgaaatgtgg ccactgcaac aacctctcct tcctcagccc    3300
gcggccgccg atggtgcagc cgctctcccc aactgatcac cccttgggcc cgtttcaggg   3360
accctgcact gactgcagga ggaaccagcc gctgccgctg gtctcgccga catcaaatga   3420
gggtagccca agagcaccct tcgttgtgaa gcccccagag aagaaacacc gcctcccatc   3480
tgcttacaac cgcttcatga gggaggaaat acagcgtatc aaagctgcca agccagatat   3540
ccctcacagg gaggccttca gcatggctgc caagaactgg gcgaagtgcg accccgctg    3600 ctcatcgacg gtttccacct ccaacagcaa ccccgagccc agagtagtag ctgctcccat   3660
tcctcatcag gagagggcca acgagcaggt ggtcgagagc ttcgacatct tcaagcagat   3720
ggagcgcagc ggctagggcg gcggcggcgg ccggagccgg cggcgatctt tatcggcggt   3780
gaagctcgta tgaagctagc tagcctgcgg taccgctcgt atgaagctag ctagcctgca   3840
ggccggccac tggggagagt accaaatttc agatccccct tattatcacc gtcgtcagct   3900
```

-continued

```
cagctcatgc atgcatgctc atcgttcccc tttagcatat atctgtgctc gttttgtgtt    3960
tattagttaa ttatgtttga tcttgttaat ttgttgttgc atggagtatg taccccctat    4020
aagacccagc tgctgctacc gtacgatata cgtacgtatg ctatatattt gtcatcttat    4080
aaatcgatgt gtgcaaagta tatgtcatgt gttcaagttt catactatag ttgacaactg    4140
atataattaa ttatcatatg taaaatacgc atgtttgcag gttttcacat atataaacac    4200
gcaatcagta gtcagtgcag atctatctct atatatgtga aatacaatta tctgtaaatt    4260
tatttttcag ataaaggaga tattttactg aagatagcac cataccactt tgaaatgaat    4320
gtttgccata agtaatttgg aggattcaat ttcctaatta aggaaaaatt ttcctataga    4380
gcccttttat tcataggaag gataggaatt ttttcataaa ggattgcact gctatggttc    4440
aattttatag gggaaaaata agcaagaggt caaatctctt ggaaactttg ctttcctttg    4500
ttagttccta caatgctagc gaagagctcc ttttcatctt tcctgcgctt ttttgtacg     4560 attaaagaaa catgcaacta cacaatttct gcattttttt cctttcttg tgttttttct     4620 atcttgcgtt tcatagggcc ggggccggtt gctcaaatac tctcagcttg ccttacatat    4680
gtgcatcatt caggctgacc ttggtgtggt tagcaaggtg taatagtggt tgtttggttg    4740
catgtattag tttaacctgg ttttatatga ggtgttgttt cattggttgg atcgatatgt    4800
gaaaacttgt atgcatggta ttcgtttggt tggataaatg aaccttgagt atactcatct    4860
ttctatgtgg atggtaagat tatccctact acccataaat agaaatatta ccaagtgcaa    4920
gatactctaa attattataa aatacacaca tttcagatat aaatgcagct aagtcaaatg    4980
cgatcgccta cacatgaaat cagcagattt gaattagagt gtggttctag aaatatcagt    5040
catcctaaaa taggtatatc cctcaaacca agagacaact agtcgagatt ccttcacagt    5100
tgtacagggc tatttgaaat atgactgtac ttgatatgca acttttttctc tatttctaca    5160 aatacatttg tattttccat acatttgtag ctacaatctg gtcccaccat gatggatggt    5220
gtagatagct ctctttttct tcaattaaca tattcttgag aatgaatggt agcttctctt    5280
tttttcttcc aattaacata ttcttaagag tgagtggtag cttttttag ccttatctaa     5340 aaaaatatga ttgataggt acgaatttcc ctttaggtta ctctgccaaa acaaaagata     5400
attgcaacaa atatatatgg ctggat                                         5426
```

<210> SEQ ID NO 21
<211> LENGTH: 6036
<212> TYPE: DNA
<213> ORGANISM: Oryza sativa Indica

<400> SEQUENCE: 21

```
cagtaaaagg cagcccatca taagctttca ttaattagcg gtacgtgtac ttttttcactg    60 aagctaggag catgcctaaa cgtacctgca actctcatgt gaaaaactca cctactaaca   120
taatcgatta gtcacgagtg cataatgaac acatatagct agtgtcgatc ggccgtatca   180
tcaaagtatg ttatctggac ctacaataat cgaccagctt atcgattgaa agacaaaaag   240
gttgtacgta tagtttgcta ggtagcattg gtacgttgta ctccttatat attgtcaaat   300
gacttgatat aaagtatgta gtagcacata taaggcacg caacagttgc tactttccca    360
gcttgctgtc tgagtgatct ctgaactgtt cttttgttct caatgaacaa taaacataaa   420
agcgatgtta tatatcattt ggccctgaat gttagtgcag atattaacat atatatagat   480
actcgtgcat catggatgca tcaagataaa cctaaccgca aaaacatttg catgcatgta   540
tgcacacata tccttaaaaa atatccgtgc ttgcttaatt tgattattgt ttcattattt   600
```

```
gcatatataa gaagccaaat gaagatcagt tagctccttt tttacataaa tatggttgga    660
ccagcagctc taaattctaa tccaatacta gaaagtgaag ttttattcgc aactgaaaac    720
accagtggcg aaaacaacag ccaaacaaca tgttaataat tagatcgatc ccctccctca    780
cacacacccc ccgtggcgtc gccatcggag cttctgttca tgtgtctccg atctgcagca    840
gagctttgcc ttttttaattt gtccggagat gcatgcatcg atcgatccaa acagctcgat    900
cgatcgatcg atctcgaccg cacatcggtc catcgatcga tcgatcgacc gaacatagga    960
tcatgttggg ttttaatgtt tctaattcgt acgaggacac aatatacatc gatcgatccg   1020
tggcgtacgt gtgcgtcgtc gtacaagaag cagtcccatg cactaagctt ctcgtatgta   1080
cagtgctcat gagtcgtaca tacatcctct tctaatgcta agtcacacac atgtacacac   1140
gctgatcatg ctcgatctag tcaagaccaa acaagctggc agcaaccaat gatcgatcta   1200
gtgaaatgtc tcgatcgatc cgccatcgac ttccttgcag tttccaacag ggtaattact   1260
taacacagac gataattctg ttaattagtt accatgtatg ggtatgcgta tcaattaatt   1320
tatgtagtaa atgtccacga tcagcttttc caaatactct taactactat aatttatctg   1380
aatttacttc ttctaaaaca ctcctaaaaa agattggaag tacactagtc acgcataatc   1440
aatagaaata tttttattat taatttact aatgcgattt ttatttgaaa aatcatatac   1500
ttatttttca tatatttata tttaaagaat tatctataag aaaattatta ttattgaaat   1560
cgagccagcc caactggtgt tatattaaga agagaaaata tgtatacaca aggtgctgtc   1620
aactactccc tccattttat attgtagtcg ttttactctt tttttcttgt caaactttat   1680
caaatttgac caattttata gaaaaaatta gcaacatata aaatatcaaa ttagtttcat   1740
taaatcgaac attaaatata ttttaataat atgtttgttt tatgttgaaa atactactat   1800
atttttctat aaatttaatc aaacttgaaa aagtttgact aagaaaaaag tcaaacgact   1860
tataatatga aatggaggga gtaattacaa aataaaactg agaaacctac tacattcctc   1920
aacaactcaa atgccagtta aggaagatat tctctaaaga tttcacacca cacaagctcc   1980
aaagtttcat ttccgatcct ccatagaaaa agaaactcc tagatatttc aattttcaaa    2040
aaacatttca aaaatctata aactgcagag attattttag gtgctctgag aactaacacc   2100
tagatattta attaggaacc tggctagcta ggggtatatg tcaagcagta ccggtactat   2160
cttccgagtc agagagagag ggagcaattg gaccattcac aatttgaggg cacagtacaa   2220
ggcacaactg gatgggatgt agtactactg tggcttcgcc accggatcgg atggacacca   2280
ctctagctag ttactgtaag catatgctat agctagctat aggagcaaac atatactgtt   2340
cccatagcct cgagatgcat atgatattac gatgtgtaga gtacatgtac acatatggag   2400
agagagagag agagagagag atagaagaga cctgtcagat cactatgctg agttatacat   2460
atatacgtac atgaaaaagt cttctctacac gttataagag aatatcccgt gcttcttaca   2520
caccatctct atattttttc aaaaagagaa attttaccgt tcttgagaaa atatcaaggt   2580
actaaacgtt aacgttagta aatatggttc actaggtatc ttttttaatga tggtaaaatt   2640 accatttttaa aaaagatgtt tctcttttc gttcgacaa gatagagcgg tgtatgttga   2700
tatatccatc catccaacca tggatctcat ctcgctatct atcttagctt tgcttgcaac   2760
atttgcctcg aaagaaagaa ataaagaaaa ggaaaaataa aaactttct ggtgctcgct   2820 ctcccgatca ctgtggttgg tctcgtgcgt acggggtcca tgtgtgcgtg ggacccctc    2880 gccattattg caacaataga aaccctaccc catccttcct ctctcccgct gtgcccaact   2940
```

```
ctccccccc  cctctctttc  tctctcctcc  ttcccgtctt  cttcctccgg  cctcttctcc  3000
tcttattgcc  cttgattcca  gtaaaaggca  gcccatcata  agctttcatt  aattagcggt  3060
acgtgtactt  tttcactgaa  gctaggagca  tgcctaaacg  tacctgcaac  tctcatgtga  3120
aaaactcacc  tactaacata  atcgattagt  cacgagtgca  taatgaacac  atatagctag  3180
tgtcgatcgg  ccgtatcatc  aaagtatgtt  atctggacct  acaataatcg  accagcttat  3240
cgattgaaag  acaaaaaggt  tgtacgtata  gtttgctagg  tagcattggt  acgttgtact  3300
ccttatatat  tgtcaaatga  cttgatataa  agtatgtagt  agcacataat  aaggcacgca  3360
acagttgcta  ctttcccagc  ttgctgtctg  agtgatctct  gaactgttct  tttgttctca  3420
atgaacaata  aacataaaag  cgatgttata  tatcatttgg  ccctgaatgt  tagtgcagat  3480
attaacatat  atatagatac  tcgtgcatca  tggatgcatc  aagataaacc  taaccgcaaa  3540
aacatttgca  tgcatgtatg  cacacatatc  cttaaaaaat  atccgtgctt  gcttaatttg  3600
attattgttt  cattatttgc  atatataaga  agccaaatga  agatcagtta  gctccttttt  3660
tacataaata  tggttggacc  agcagctcta  aattctaatc  caatactaga  aagtgaagtt  3720
ttattcgcaa  ctgaaaacac  cagtggcgaa  acaacagcc   aaacaacatg  ttaataatta  3780
gatcgatccc  ctccctcaca  cacaccccc   gtggcgtcgc  catcggagct  tctgttcatg  3840
tgtctccgat  ctgcagcaga  gctttgcctt  tttaatttgt  ccggagatgc  atgcatcgat  3900
cgatccaaac  agctcgatcg  atcgatcgat  ctcgaccgca  catcggtcca  tcgatcgatc  3960
gatcgaccga  acataggatc  atgttgggtt  ttaatgtttc  taattcgtac  gaggacacaa  4020
tatacatcga  tcgatccgtg  gcgtacgtgt  gcgtcgtcgt  acaagaagca  gtcccatgca  4080
ctaagcttct  cgtatgtaca  gtgctcatga  gtcgtacata  catcctcttc  taatgctaag  4140
tcacacacat  gtacacacgc  tgatcatgct  cgatctagtc  aagaccaaac  aagctggcag  4200
caaccaatga  tcgatctagt  gaaatgtctc  gatcgatccg  ccatcgactt  ccttgcagtt  4260
tccaacaggg  taattactta  acacagacga  taattctgtt  aattagttac  catgtatggg  4320
tatgcgtatc  aattaattta  tgtagtaaat  gtccacgatc  agcttttcca  aatactctta  4380
actactataa  tttatctgaa  tttacttctt  ctaaaacact  cctaaaaaag  attggaagta  4440
cactagtcac  gcataatcaa  tagaaatatt  tttattatta  attttactaa  tgcgattttt  4500
atttgaaaaa  tcatatactt  attttttcata  tatttatatt  taaagaatta  tctataagaa  4560
aattattatt  attgaaatcg  agccagccca  actggtgtta  tattaagaag  agaaaatatg  4620
tatacacaag  gtgctgtcaa  ctactccctc  cattttatat  tgtagtcgtt  ttactctttt  4680
tttcttgtca  aactttatca  aatttgacca  attttataga  aaaaattagc  aacatataaa  4740
atatcaaatt  agtttcatta  aatcgaacat  taaatatatt  ttaataatat  gtttgtttta  4800
tgttgaaaat  actactatat  ttttctataa  atttaatcaa  acttgaaaaa  gtttgactaa  4860
gaaaaaagtc  aaacgactta  taatatgaaa  tggagggagt  aattacaaaa  taaaactgag  4920
aaacctacta  cattcctcaa  caactcaaat  gccagttaag  gaagatattc  tctaaagatt  4980
tcacaccaca  caagctccaa  agtttcattt  ccgatcctcc  atagaaaaaa  gaaactccta  5040
gatatttcaa  ttttcaaaaa  acatttcaaa  aatctataaa  ctgcagagat  tattttaggt  5100
gctctgagaa  ctaacaccta  gatatttaat  taggaacctg  gctagctagg  ggtatatgtc  5160
aagcagtacc  ggtactatct  tccgagtcag  agagagaggg  agcaattgga  ccattcacaa  5220
tttgagggca  cagtacaagg  cacaactgga  tgggatgtag  tactactgtg  gcttcgccac  5280
cggatcggat  ggacaccact  ctagctagtt  actgtaagca  tatgctatag  ctagctatag  5340
```

-continued

```
gagcaaacat atactgttcc catagcctcg agatgcatat gatattacga tgtgtagagt    5400
acatgtacac atatggagag agagagagag agagagagat agaagagacc tgtcagatca    5460
ctatgctgag ttatacatat atacgtacat gaaaaagtct ttctacacgt tataagagaa    5520
tatcccgtgc ttcttacaca ccatctctat attttttcaa aaagagaaat tttaccgttc    5580
ttgagaaaat atcaaggtac taaacgttaa cgttagtaaa tatggttcac taggtatctt    5640
tttaatgatg gtaaaattac cattttaaaa aagatgtttc tcttttcgt ttcgacaaga     5700 tagagcggtg tatgttgata tatccatcca tccaaccatg gatctcatct cgctatctat    5760
cttagctttg cttgcaacat ttgcctcgaa agaaagaaat aaagaaaagg aaaaataaaa    5820 actttctgg tgctcgctct cccgatcact gtggttggtc tcgtgcgtac ggggtccatg     5880
tgtgcgtggg acccctcgc cattattgca acaatagaaa ccctacccca tccttcctct     5940
ctcccgctgt gcccaactct cccccccccc tctctttctc tctcctcctt cccgtcttct    6000
tcctccggcc tcttctcctc ttattgccct tgattc                               6036
```

<210> SEQ ID NO 22
<211> LENGTH: 1342
<212> TYPE: DNA
<213> ORGANISM: Oryza sativa Indica

<400> SEQUENCE: 22

```
tataaatcga tgtgtgcaaa gtatatgtca tgtgttcaag tttcatacta tagttgacaa      60
ctgatataat taattatcat atgtaaaata cgcatgtttg caggttttca catatataaa     120
cacgcaatca gtagtcagtg cagatctatc tctatatatg tgaaatacaa ttatctgtaa    180
atttattttt cagataaagg agatatttta ctgaagatag caccatacca ctttgaaatg    240
aatgtttgcc ataagtaatt tggaggattc aatttcctaa ttaaggaaaa attttcctat    300
agagcccttt tattcatagg aaggatagga attttttcat aaaggattgc actgctatgg    360
ttcaatttta taggggaaaa ataagcaaga ggtcaaatct cttggaaact ttgcttcct     420 ttgttagttc ctacaatgct agcgaagagc tccttttcat cttcctgcg ctttttttgt     480 acgattaaag aaacatgcaa ctacacaatt tctgcatttt tttccttttc ttgtgttttt    540
tctatcttgc gtttcatagg gccgggccg gttgctcaaa tactctcagc ttgccttaca     600
tatgtgcatc attcaggctg accttggtgt ggttagcaag gtgtaatagt ggttgtttgg    660
ttgcatgtat tagtttaacc tggttttata tgaggtgttg tttcattggt tggatcgata    720
tgtgaaaact tgtatgcatg gtattcgttt ggttggataa atgaaccttg agtatactca    780
tctttctatg tggatggtaa gattatccct actacccata aatagaaata ttaccaagtg    840
caagatactc taaattatta taaaatacac acatttcaga tataaatgca gctaagtcaa    900
atctacacat gaaatcagca gatttgaatt agagtgtggt tctagaaata tcagtcatcc    960
taaaataggt atatccctca aaccaagaga caactagtcg agattccttc acagttgtac   1020
agggctattt gaaatatgac tgtacttgat atgcaacttt ttctctattt ctacaaatac   1080
atttgtattt tccatacatt tgtagctaca atctggtccc accatgatgg atggtgtaga   1140
tagctctctt tttcttcaat taacatattc ttgagaatga atggtagctt ctctttttt    1200 cttccaatta acatattctt aagagtgagt ggtagctttt tttagcctta tctaaaaaaa   1260
tatgattgat agggtacgaa tttccctta ggttactctg ccaaaacaaa agataattgc    1320
aacaaatata tatggctgga tt                                             1342
```

<210> SEQ ID NO 23
<211> LENGTH: 5693
<212> TYPE: DNA
<213> ORGANISM: Oryza sativa Indica

<400> SEQUENCE: 23

```
aaagatgtct aaatagctat aaatgggtaa gcaagatagc aaagaaggcc agtggccttt      60
gcagctaagc tagctagcta gcccttcttc ctctctttcc tgctttccct ttgccttctc     120
ctattaatcc tctgcacctc acacagcagc agaaaaccca ccaactggag ctctcctttc     180
ctactccaag aaacgaaggt agagaaagaa agatcagatc agcttcagga ccaattttag     240
ctaggttata tatctctttg cgtgctaatg tgttttagtt atctgggtgt gtgtagagtt     300
ctttgttaag gcactgattc agctgcagtt tagattcaag tttgtatgtt ctctctttga     360
ggaaaagaaa ccctttttcct gtgcttcgag ttcttgcaaa gagaaactgt gatgcttggc     420
ttccagtttg atgcttcttt gttcagattg gaaattcttc ctagcttctt tctctattta     480
tgtagcaagg attctttccg gcccagtgat cctggtttct tttggaaggt ttcagttttt     540
tcgttctttc ttgaaatttc tcttcttgcc ttaggcagat ctttgatctt gtgaggagac     600
aggagaaaag gaagaagcta gtttcctgcg gccgacctct tgcttctcac tttgtgatga     660
gttttctttg gtcaattctt agctagatat gttaagatag ttagttaagc aaatcgaaat     720
tgctagcttt tccatgcttt cttaaacatg attcttcaga tttggttggt tctttttttt     780
ccttttttgtg gagacgtgct gttcttgcat cttatccttc ttgattcatc tacccatctg     840
gttctttgag ctttctttttt cgcttcttcc cttcattatt tcgagcaatc tctgcacatc     900
tgaaagtttt gtttcttgag actacttttg ctagatcttg tttactcgat cactctatac     960
ttgcatctag gctcctttct aaataggcga tgattgagct ttgcttatgt caaatgatgg    1020
gatagatatt gtcccagtct ccaaatttga tccatatccg ccaagtcttt catcatcttt    1080
ttctttcttt tttatgagca aaaatcatct tttcttttca agttcagct tttttctctt     1140
gttttacccc tctttagcta tagctggttt cttattcctt ttggatttac atgtataaaa    1200
catgcttgaa tttgttagat cgatcacttt atacacatac tatgtgaatc acgatctcag    1260
atctctcagt atagttgaat tcattaattt cttagatcga tcagcgtgtg atgtagtact    1320
gtaaatcact actagatctt tcatcagtct cttttctgca tctatcaatt tctcatgcaa    1380
gttttagttg tttctttaat ccggtctctc tctcttttt aatcagctga gagtttgtgc     1440
tgttctttaa tcattaccag atctttcatc agtactctct cttctgcatc tatcaaactt    1500
ctcatgcaat gttttttgctg ttctttgatc tgatctctgg tctccttttt tgttgatcag    1560
ttgagagcaa gaagacatgg ggaggggcag gattgagatc aagaggatcg agaacacgac    1620
aagccgccag gtgaccttct gcaagcgccg caacggactt ctcaagaagg cgtatgagct    1680
ctccgtcctc tgcgatgccg aggtggctct catcgtcttc tccagccgtg gccgcctcta    1740
cgagtactcc aacaacaaca agtatgtact tgctgtaaat atattggctt aattttgtac    1800
tcagttcttg aaactaactt gctgattgct ttgtttccct tcgtgtcatt tcatgctcag    1860
cgtgcttgtt gtgttgcttt atttgtggct aatagtttgt tattgagtaa agtttagtt    1920
gtggttaaaa ctgactcttg gtaaatattt tagaatgagt ttaatattat acacattctt    1980
agatgatatg tgaattactt aactcaaggt gtgaaatgat ttaggaaaaa tgttagagtt    2040
tatcataaaa actcatcaag atgtatatgt ttgctcatca gctagctgta agattaatgc    2100
tgaaaatgtt gtcctgttta gttacttgaa aaaggactat tctgttctaa ttttcttagt    2160
```

```
cttatggtca gaaggcttta ctaaagtcca tttatatatc ctgcttgcta aattgatttt    2220
gctggaaaga attaaccatg tatgcatgga ctttaatttc atctgtgcat gtaacaagac    2280
ttgcttactt ttttcagtta tcatctactc agattacgaa ataaaattgt aagatttatt    2340
tcaaactata tgcatggtac tatatatggt gatttgtcat gcatgcatga ttatattgtt    2400
tttgtatcta aataaagtta ctctcttaac ctccatggaa aattccttag ctattgctca    2460
tcattttcaa agtgagatgt gtgaattaga tatgtacaca catattaagg ggaggctatt    2520
tgaaagatac attagaatcc ccttccaatt cattcatgca tgcagtcaaa taattattta    2580
aagtttgcaa agtctcattg tttttataca tgtcaaattc atttgcaatc tctctcgagt    2640
acatgtacat gagtatgcat gcatgcaaac tttaaataat atatatcagt gctatcagta    2700
cttgagcagc tagcaaagcc actgccatct tttatcatat tttattctcc acagttcaca    2760
caacacacat catatcatgc acagcaagga agctcagtct cctgtcaatg ttgtatgttc    2820
agtagatagt tcaccctaga aactagctgt caagagtttc cttttccttg cttctccata    2880
caccgataca catatagaca ccatggacat gcatgagaag aacttgcacc aagctagaaa    2940
ctgcagcaac gtcctcccat attcgctgtg tttgctcttc tccggtgcaa agttgtgcat    3000
cagttaataa gccaatggcc atccatctga ccatctctct ttctctctag ctcgtgtata    3060
ctcatttcat tccgttcttg tgttcacttc aacacagttc ttgcagctag agacagcatg    3120
cattccaatg gctacctttc ttctgcacaa ttttatgctg aagtaattaa acgcttgctc    3180
ctcacatgca ttatttctgc attcatgaca tgtatagtca tgtgtgttgc atttcttctc    3240
ttgttggcat atatgaacac actacattac catgcatgca caattatcag tatttatgtt    3300
gtagtgttga gagagtacca ctcgactgat gggatatata ctgcagtgtg aaggctacaa    3360
ttgacaggta caagaaggcg catgcttgtg gctcaacttc tggtgcacct ctcatagagg    3420
tcaatgctca ggtaacccat atatatgttg ctgctttgtt aattaccttc ttctattcat    3480
tttgccttag tttcagttaa attaatttgg tgactattct aaaaccaagg catattcata    3540
catataaagt gagagcatat agatgccttg cattttaagt attttatata cttttttgtgg   3600 taggtaattg actgctgcat tatattaatt tgttagtttc atcagggtat ggcttgatct    3660
ttgtgcttat atacattcat gtgttatagc tatacagcat caatctttac gacaagattg    3720
aattcataat taatgtagta tgtgaaccac ttggagattg cctaatgcct agtctgcaat    3780
tctgcactga agttctccat atatttgtct ttctctgagt ttaagagtat acttttctta    3840
gaaactgtaa gtgtaccctt tgtggctag tggcttgcaa tttaaagtta gtgactgaag    3900
agaacaaaca aaattcacaa aataaacttc aatgtaaaag catgaatgca gtcattctgt    3960
tgcactacaa ttaaggttac tgttactttt ttttttgct gatcaattag agctacatga    4020
taaacgtaat taaatctgat cgatcgtctt gttaattgtc ttgtctgaag caatactacc    4080
agcaggagtc tgccaaactg cgccaccaga ttcagatgct gcaaacacc aacaaataag    4140 tgcctaatac taatacacaa ttttatatc tgccattcaa gaaacacatg tgtatatatc    4200
gatgataata ttgaaaagag attactttac agaatcaatg tgatgacctg gaaatacccta   4260 ttttcgtttg gtttgttttc ctatgtgaaa ggcacctggt tggcgataat gtgagcaacc    4320
tgtcactgaa ggagctgaag caacttgaaa gccgcctgga gaaaggcatt tcaaagatca    4380
gagccaggaa ggtaaacaac tatatataaa ataccatttt cacatgaaca ttcaattacc    4440
aacctcatgg tgtcaccttt agaacaaaat ctcagtgctg ttagatatat atgatcacct    4500
```

```
tgatttactt tgtttgaaca attcttcagt ttctgatgca atgttaactt actaagtggc    4560
cttaaaaatg tacaaattaa ctgttaatcc ttatttgttt aattttatct cagaatgaac    4620
tgctggcttc agagatcaat tacatggcca aaagggtatg tgtgttacta gaattgcatc    4680
ttacatacaa ttgtacatac tgatcaatga ttgcaaactc ctttcttaat cctctattct    4740
ttttacctga ttgcataatt cttgttagca ttactcattt gcaatgttct tgtcatgatt    4800
tcaggagatt gagcttcaga acgacaacat ggacctcaga accaaggtaa atacatatca    4860
ggtgactgca agaaatcaga accaacttcc aatttcttgt ttgcaaatca gagattaatt    4920
agctagctat ttgtttaaat taatttgaac aaatagctag ctaattaatc tataaagctt    4980
gacgaaaaga acaatatatc tctacatcaa cgacacatct atctctacta tacgttgatg    5040
agagatcatg tgcacacttg cagattgctg aggaggagca gcagctgcag caggtgacgg    5100
tggcccggtc ggccgccatg gagctgcagg ctgcggcggc ggcgcagcag cagcagcaga    5160
atccgttcgc ggtggcggcg gcgcagctgg acatgaagtg cttcttcccg ttgaacctgt    5220
tcgaggcggc ggcgcaggtg caggccgtgg cggcgcagcg ccagcagatc atccccaccg    5280
agctcaacct cggctaccac caccaccttg ccattcccgg cgccgccgcc gccgacgcgc    5340
cgcctcctca cttctgaacc tcatgaactt cattctgcac cggcctgctg ccatggatat    5400
gatgatcagc tcatcttcta tatcttatgc tgttatgcag acagacacta ctgatgtggc    5460
tatatatata gtatttgtgt gctgctgcat tttgttaatc ccttataaat tgctacttaa    5520
ttatctcatg gagaattgga gagaccaaat gggcagagct agctagttag ctgtgcccaa    5580
ttaagaagct aaatctatca gaagtgtgta ctgatgagtg atgagtattt ttcttcattt    5640
gggatcaaat taaactaagt aaaacatata tatttgactt atgttttacg tgc           5693
```

REPRODUCTION OF FEMALE STERILITY LINES AND ITS APPLICATION IN HYBRID SEED PRODUCTION

The present application is a National Stage Application of PCT/CN2014/095240, filed Dec. 29, 2014, which claims priority of Chinese Patent Application No. 201410001109.7, filed Jan. 2, 2014. The entirety of the aforementioned applications is incorporated herein by reference.

TECHNICAL FIELD

The present invention relates to the fields of plant molecular biology and breeding, in particular relates to a method for producing hybrid rice, more particularly relates to propagation and maintenance of female sterile lines and the use thereof in producing hybrid rice.

BACKGROUND

Rice female sterile types are numerous, which results from interaction between different gene mutations and ambient conditions. The researches on the rice female sterility are limited and there are still many scientific questions needed to be further investigated and studied. At present, the researches on the rice female sterility mainly focus on cytological analysis, and the researches in genetics and molecular biology are relatively few.

Breakthrough in rice breeding often started from the development of specific breeding materials, such as aijiaonante rice found by HONG, Qunying and HONG, Chunli in Guangdong, a wild abortive male sterile plant found by LI, Bihu in Hainan, and agricultural reclamation-58 sterile plant found by SHI, Mingsong in Hubei. The discovery of these special mutants provides a solid material basis for genetic breeders, and raises multiple tides in rice breeding for dwarfness and hybridization breeding in our country. However, with the in-depth genetic breeding researches and application in rice, the difficulties in exploration and innovation of breeding materials are increasing continuously.

In the prior art, there are "three-line" or "two-line" methods for hybrid rice, and due to the restriction of parent fertility, it is difficult to produce hybrid seeds via mechanization. Therefore, labor force consumption limited the production scale of hybrid rice seeds, and resulted in high cost of seeds, which restrict the promotion and application of hybrid rice.

If a female sterile line is used as a male parent during hybrid seed production, the female sterile male parent can pollinate the male sterile line (female parent) to generate hybrid seeds, and the female sterile line (male parent) itself cannot produce seeds, cannot produce seeds by self-pollination to affect the purity of hybrid seeds, and thus needs not be removed after pollination. Therefore, the male sterile line (female parent) and the female sterile line (male parent) can be mixed to sow in production, which can improve the cross pollination efficiency (i.e. hybrid species seed production efficiency) in natural conditions and reduce artificial pollination. The male parent plants need not to be removed after pollination, which reduces the labor cost during seed production and facilitates mechanized seed production. Therefore, the problems of two-line or three-line methods that the plants need to be intercropped in rows and the male parental plants need to be cut off after pollination, which costs a great of human cost, can be overcome by the present technology.

SUMMARY

The present invention provides a method for propagating a homozygous recessive nuclear female sterile line, comprising:
(a) providing a first plant, wherein a gene regulating the female organ development in the first plant has a homozygous recessive mutation, and the first plant shows female sterility;
(b) introducing an exogenous construct into the first plant to form a second plant, the exogenous construct comprising:
 i) a first nucleotide sequence, comprising a nucleotide sequence of a gene when mutated will result in female sterility in a plant, and when expressed in the first plant will recover normal female organ development of the first plant;
 ii) a second nucleotide sequence, when expressed, which will inhibit the formation or function of fertile male gametes in the second plant;
 iii) a third nucleotide sequence, when expressed, by which whether a plant contains an introduced construct or not can be distinguished; and
(c) self-pollinating the second plant, wherein in the generated offsprings, one half is the first plant with homozygous recessive nuclear female sterility which does not contain the exogenous construct, and the other half is the second plant containing the exogenous construct.

In the present invention, the first nucleotide sequence mentioned in the above method for propagating the homozygous recessive nuclear female sterile line can be OsFMS2 or OsFMS1. More preferably, the first nucleotide sequence is operably linked with a fourth nucleotide sequence, and the fourth nucleotide sequence can drive the first nucleotide sequence to express in the plant female organ.

The second nucleotide sequence mentioned in the above method for propagating the homozygous recessive nuclear female sterile line is selected from a group consisting of nucleotide sequences of a maize α-amylase gene, auxin, rot B, a cytotoxin associated gene, diphtherin, a DAM methylase, and PA. The second nucleotide sequence is operably linked with a fifth nucleotide sequence, and the fifth nucleotide sequence can drive the second nucleotide sequence to express in male gametes. Specifically, the fifth nucleotide sequence is selected from a group consisting of a polygalacturonase 47 gene, a Zm13 gene, a pectin methylesterase gene, a calmodulin binding protein gene, an actin depolymerizing factor gene, a prolfilin gene and a regulatory region of sulfated pentapeptide phytosulphokine gene.

The third nucleotide sequence mentioned in the above method for propagating the homozygous recessive nuclear female sterile line is selected from a group consisting of a chloromycetin resistance gene, a hygromycin resistance gene, a streptomycin resistance gene, a miramycin resistance gene, a sulfonamide resistance gene, a glyphosate resistance gene, a glufosinate resistance gene, a red fluorescence gene, a cyan fluorescent protein gene, a yellow fluorescent protein, a luciferase gene, a green fluorescent protein gene, anthocyanin p1 or a blue fluorescent protein, and other genes. The third nucleotide sequence is operably linked with a sixth nucleotide sequence, and the sixth nucleotide sequence is a promoter specifically expressed in a seed or endosperm, such as END2 or LTP2.

The present invention also provides a method for producing seeds from a female sterile plant, the method comprising:

(a) providing a first plant, wherein a gene regulating the female organ development of the first plant has a homozygous recessive mutation, and the plant shows female sterility;
(b) introducing an exogenous construct into the first plant to generate a second plant, the exogenous construct comprising:
  i) a first nucleotide sequence, comprising a nucleotide sequence of a gene when mutated will result in female sterility in a plant, and when expressed in the first plant will recover the female fertility of the plant;
  ii) a second nucleotide sequence, when expressed, which will inhibit the formation or function of fertile male gametes in the second plant;
  iii) a third nucleotide sequence, when expressed, by which whether a plant contains an introduced construct or not can be distinguished; and
(c) self-pollinating the second plant to produce seeds containing or not containing the exogenous construct.

The method for producing seeds from a female sterile plant as described above, wherein the first nucleotide sequence is OsFMS2 or OsFMS1. The first nucleotide sequence is operably linked with a fourth nucleotide sequence, and the fourth nucleotide sequence can drive the first nucleotide to express in ovule, carpel or other plant female organs.

The method for producing seeds from a female sterile plant as described above, wherein the second nucleotide sequence is selected from a group consisting of nucleotide sequences of a maize α-amylase gene, auxin, rot B, a cytotoxin associated gene, diphtherin, DAM methylase, and PA. The second nucleotide sequence is operably linked with a fifth nucleotide sequence, and the fifth nucleotide sequence can drive the second nucleotide sequence to express in male gametes. More specifically, the fifth nucleotide sequence is selected from a group consisting of the regulatory regions of polygalacturonase 47 gene, Zm13 gene, pectin methylesterase gene, calmodulin binding protein gene, actin depolymerizing factor gene, prolfilin gene and sulfated pentapeptide phytosulphokine gene.

The method for producing seeds from a female sterile plant as described above, wherein the third nucleotide sequence is selected from a group consisting of a chloromycetin resistance gene, a hygromycin resistance gene, streptomycin resistance gene, a miramycin resistance gene, a sulfonamide resistance gene, a glyphosate resistance gene, a glufosinate resistance gene, a red fluorescence gene, a cyan fluorescent protein gene, a yellow fluorescent protein, a luciferase gene, a green fluorescent protein gene, anthocyanin p1 or a blue fluorescent protein, and other genes. The third nucleotide sequence is operably linked with a sixth nucleotide sequence, and the sixth nucleotide sequence is a promoter which is specifically expressed in a seed or endosperm, such as END2 or LTP2.

The present invention also provides a construct, wherein the construct comprises:
  i) a first nucleotide sequence, comprising a nucleotide sequence of a gene when mutated will result in female sterility in a plant, and when expressed in the first plant will recover the female fertility of the plant;
  ii) a second nucleotide sequence, when expressed, which will inhibit the formation or function of fertile male gametes in the second plant; and
  iii) a third nucleotide sequence, when expressed, by which whether a plant contains an introduced construct or not can be distinguished.

In the present invention, the first nucleotide sequence contained in the above construct is OsFMS2 or OsFMS1. The first nucleotide sequence is operably linked with a fourth nucleotide sequence, and the fourth nucleotide sequence can drive the first nucleotide sequence to express in ovule, carpel or other plant female organs.

In the present invention, the second nucleotide sequence contained in the above construct is selected from a group consisting of nucleotide sequences of a maize α-amylase gene, auxin, rot B, a cytotoxin associated gene, diphtherin, and DAM methylase. The second nucleotide sequence is operably linked with a fifth nucleotide sequence, and the fifth nucleotide sequence can drive the second nucleotide sequence to express in male gametes. More specifically, the fifth nucleotide sequence is selected from a group consisting of the regulatory regions of polygalacturonase 47 gene, Zm13 gene, pectin methylesterase gene, calmodulin binding protein gene, actin depolymerizing factor gene, prolfilin gene and sulfated pentapeptide phytosulphokine gene.

In the present invention, the third nucleotide sequence contained in the above construct is selected from a group consisting of a chloromycetin resistance gene, a hygromycin resistance gene, streptomycin resistance gene, a miramycin resistance gene, a sulfonamide resistance gene, a glyphosate resistance gene, a glufosinate resistance gene, a red fluorescence gene, a cyan fluorescent protein gene, a yellow fluorescent protein, a luciferase gene, a green fluorescent protein gene, anthocyanin p1 or a blue fluorescent protein, and other genes. The third nucleotide sequence is operably linked with a sixth nucleotide sequence, and the sixth nucleotide sequence is a promoter which is specifically expressed in a seed or endosperm, such as END2 or LTP2.

The present invention also provides a method for hybrid seed production using a recessive nuclear female sterile line, the method comprising: mixed sowing a recessive nuclear female sterile plant and a male sterile plant to produce hybrid seeds, characterized in that the recessive nuclear female sterile plant contains a nucleotide sequence shown as SEQ ID NO: 5, 19 or 23.

The present invention also provides a nucleotide sequence, characterized in that the nucleotide sequence is shown as SEQ ID NO: 5, 19 or 23, and the mutation of such sequence will result in female sterility in a plant.

BRIEF DESCRIPTION OF THE DRAWINGS

FIG. 6 shows an alignment of OsFMS2 gene cDNA sequences in wild-type Huang Huazhan and osfms2 mutant, wherein the polymorphic sites are indicated in bold.
FIG. 7 shows an alignment of OsFMS2 gene cDNA sequences in wild-type Huang Huazhan and Nipponbare, wherein the site polymorphism is shown in red bold.
FIG. 8 shows an amino acid sequence alignment of OsFMS2 gene in wild-type Huang Huazhan and Nipponbare, wherein the polymorphism is indicated in red bold.
FIG. 9 is a plasmid map of an exogenous construct pFMS2.

FIG. 10 shows that a fluorescent seeds carrying the exogenous construct in FIG. 9 and non-fluorescent seeds not carrying the exogenous construct show 1:1 separation ratio.

FIG. 13 is a sequence alignment of OsFMSJ gene in the wild-type and osfms1 mutant.

FIG. 14 is an amino acid sequence alignment of OsFMS1 in the wild-type and osfms1 mutant.

FIG. 15 is a plasmid map of an exogenous construct pFMS1.

DETAILED DESCRIPTION

Figure 1:
FIG. 1 is a female sterile mutant material osfms2.

All the references described herein are incorporated herein by citation.

Unless indicated otherwise, all technical and scientific terms used herein have the same meanings as commonly understood by one of ordinary skill in the art. Unless indicated otherwise, the techniques used or mentioned herein are commonly known standard techniques for a person skilled in the art. Materials, methods and examples are only used for illustration, rather than to limit.

The terms "first" and "second" is only used for illustration, and should not be understood as indication or implication of the relative importance or implicit indication of the quantity of technical features indicated. Thus, a feature defined by "first" and "second" can explicitly or implicitly comprise one or more of the feature. In the description of the present invention, the term "a plurality of" means two or more, unless defined specifically and particularly otherwise.

The present invention aims to provide a method for effectively propagating a recessive rice nuclear female sterile line, and a strategy for developing hybridization breeding by fully using rice genetic resources and reducing the hybrid seed production cost.

The present invention provides a propagation method for keeping the homozygous recessive allelic state of the female sterile line, the method comprising: using a homozygous recessive nuclear female sterile mutant as a transformation receptor material, transforming three target genes therein, respectively being a female fertility gene which after been mutated will result in female sterility in a plant, a pollen inactivation gene and a screening gene. The female fertility gene can recover the fertility of the transformation receptor material with female sterility, the pollen inactivation gene can inactivate the pollen containing the transformed exogenous construct, i.e. lose the insemination capability, and the screening gene can be used for sorting the transgenic seeds and the non-transgenic seeds, wherein the sorted non-transgenic seeds are used as a female sterile line for production of hybrid seeds, and transgenic seeds are used as a maintenance line to produce a female sterile line and a female sterility maintenance line continuously and stably.

In the present invention, the female fertility genes are predominantly expressed in female organs. More specifically, in rice plants, the female fertility genes comprise but are not limited to OsFMS2 and OsFMS1. The present invention also provides a method for obtaining a female sterile line material, the method comprising obtaining a female sterile mutant material by technical strategy of mutating the above female fertility gene and other genes for regulating the female organ development, and thus the female sterile line material can be applied to the hybrid seed production via the method disclosed in the present invention. The "mutating" comprises but is not limited to the following methods, such as gene mutation caused by a physical or chemical method and mutagenesis caused by a chemical method comprising treatment by a mutagenic agent such as EMS. The mutation can be a point mutation, and can also be a DNA deletion or an insertion mutation, and can also be produced by gene silencing such as RNAi and site-directed gene mutation, wherein the method for the site-directed gene mutation comprises but is not limited to the method of ZFN site-directed mutation, TALEN site-directed mutation, CRISPR/Cas9 or other site-directed mutation.

In the present invention, the pollen inactivation gene can interfere with the formation or function of pollens (male gametes), more particularly comprises but is not limited to genes capable of encoding enzymes promoting the degradation of carbohydrates, or modifying enzymes, amylase, debranching enzyme and pectinase, more specifically, such as a corn α-amylase gene, auxin, rot B, a cytotoxin gene, a diphtherin gene, a DAM methylase enzyme (DNA (Adenosine-N6) methyltransferase), avidin gene, and may also be a dominant male sterility gene, or can be selected from procaryotic regulating system, etc. For example, it was indicated by Mariani, et al., Nature Vol. 347; pp. 737; (1990) that the expression of *Aspergillus oryzae* RNase-T1 or *Bacillus amyloliquefaciens* RNase (named as "barnase") induces the lysis of tapetal cells, resulting in male sterility. The chemical synthesis of RNase-T1 is described by Quaas, et al., *Eur. J. Biochem.* Vol. 173: pp. 617 (1988), and the nucleotide sequence of the barnase gene is disclosed by Hartley, *J. Molec. Biol.*; Vol. 202: pp. 913 (1988). *Agrobacterium rhizogenes* rolB gene encodes an enzyme for liberating free indole from indoxyl-β-glycoside so as to interfere with the auxin metabolism. It is indicated by Estruch, et al., *EMBO J.* Vol. 10: pp. 3125 (1991) and Spena, et al., *Theor. Appl. Genet.*; Vol. 84: pp. 520 (1992) that pollen sac-specific expression of rolB gene in tobacco produces a plant with withered pollen sacs, wherein the production of pollens is greatly reduced and the rolB gene is an example for controlling the pollen production. The nucleotide sequence of rolB gene is disclosed by Slightom, et al., *J. Biol. Chem.* Vol. 261: pp. 108 (1986). The DNA molecule encoding a diphtherin gene is available from American Type Culture Collection (Rockville, Md.), ATCC No. 39359 or ATCC No. 67011, and with regard to the examples and usage methods, reference can be made to Fabijanski, et al., E.P. Appl. No. 90902754.2, "Molecular Methods of Hybrid Seed Production". The DAM methylase gene is used in the methods discussed in U.S. Pat. No. 5,689,049 and PCT/US 95/15229, Cigan, A. M. and Albertsen, M. C., "Reversible Nuclear Genetic System for Male Sterility in Transgenic Plants", resulting in sterility. The discussion on the avidin gene, which can result in sterility, is available in U.S. Pat. No. 5,962,769 "Induction of Male Sterility in Plants by Expression of High Levels of Avidin" by Albertsen et al.

The propagation method of the female sterile line in the present invention can also comprise a screening gene for screening the transformed cells or tissues. The screening gene comprises genes imparting the antibiotic resistance or herbicide resistance, and suitable screening marker genes comprise but are not limited to: a chloromycetin resistance gene, a hygromycin resistance gene, a streptomycin resistance gene, a miramycin resistance gene, a sulfonamide resistance gene, a glyphosate resistance gene, and a glufosinate resistance gene. The screening gene may also be fluorescent screening genes, including, but not limited to, a red fluorescence gene, a cyan fluorescent protein gene, a yellow fluorescent protein gene, a luciferase gene, a green fluorescent protein gene, an anthocyanin p1 gene, a blue fluorescent protein gene, or other genes.

More specifically, according to one embodiment of the present invention, the rice recessive nuclear female sterile osfms2 mutant can be used as a transformation receptor material, and the sterile line is transformed with 3 target genes linked closely, wherein the female fertility gene OsFMS2 can recover the fertility of the transformation receptor material, the pollen inactivation gene PA can inactivate the pollen containing the exogenous gene, i.e. lose the insemination capability, and the fluorescence screening gene RFP can be used for sorting the transgenic seeds and the non-transgenic seeds, wherein the sorted non-transgenic seeds are used as a female sterile line (male parent) for production of hybrid seeds, and transgenic seeds are used as a maintenance line to produce a female sterile line and a female sterility maintenance line continuously and stably. The technique can produce a large amount of female sterile material (male parent), and the mixed sowing of the male and female parents can be performed in hybrid seed production, so as to solve the problem of plantation in row during rice hybrid seed production, improve the cross pollination efficiency (i.e. hybrid species seed production efficiency) in natural conditions and reduce the labor cost in artificial pollination; meanwhile, the male parent plant needs not be removed after pollination, thereby reducing the labor cost during seed production and facilitating mechanized seed production.

The present invention also discloses a construct, and according to embodiments of the present invention, the construct comprises: a first expression cassette containing a first nucleic acid molecule which is a female fertility gene; a second expression cassette containing a second nucleic acid molecule encoding a pollen inactivation protein. Using the construct, the rice female fertility gene and pollen inactivation gene can be efficiently introduced into a homozygous recessive nuclear female sterile rice mutant plant, so as to obtain a fertile plant carrying an exogenous gene as a maintenance line, so that the sterile lines and maintenance lines can be continuously produced conveniently by self-crossing. Furthermore, the plant not carrying the exogenous gene can be used as the male parent for hybridization, and is thus efficiently used for rice hybridization, and the resulting cross species is also non-transgenic. Furthermore, the above construct may also comprise a third expression cassette containing a third nucleic acid molecule that is a screening marker gene. Using the construct, the seeds with or without the transgene can be effectively separated, the non-transgenic seeds are used as female sterile lines for producing hybrid species, and the transgenic seeds are used as maintenance lines to produce the sterile lines continuously.

In one illustrative embodiment, the above propagation method for keeping the homozygous recessive state of the female sterile plant can also further comprise the following nucleotide sequence: an optional fourth nucleotide sequence that is operably connected with a first nucleic acid molecule and drive the first nucleotide sequence to express in a plant female organ, wherein the first nucleic acid molecule (also referred to the first nucleotide sequence) is a female fertility gene having an effect of recovering the female fertility of a female sterile line; and an optional fifth nucleotide sequence, which directs the biased expression in a male gamete, and is operably connected with the second nucleic acid molecule (also referred to the second nucleotide sequence), wherein the fifth nucleotide sequence is selected from a group consisting of a polygalacturonase 47 gene, Zm13 gene, a pectin methylesterase gene, a calmodulin binding protein gene, an actin depolymerizing factor gene, a prolfilin gene and a regulatory region of sulfated pentapeptide phytosulphokine gene, wherein the second nucleic acid molecule is pollen inactivation protein capable of inhibiting the formation or function of a fertile male gamete; and optionally a sixth nucleotide sequence which is operably linked with the third nucleic acid molecule (also referred to the third nucleotide sequence, being a screening gene) and can drive the third nucleotide sequence to express specifically in a seed or endosperm, and particularly the sixth nucleotide sequence can be promoters such as END2 and LTP2.

Thus, the above construct can be introduced into cells, tissues or organs of a plant through conventional techniques such as agrobacterium-mediated method, so as to obtain a sample which can be used for subsequent researches and hybridization. Accordingly, the present invention also discloses a rice cell, tissue or organ. According to embodiments of the present invention, the cell, tissue or organ contains the construct as described above.

The present invention also discloses a new seed breeding method. According to embodiments of the present invention, the method comprises introducing the construct described above into a first rice homozygous recessive female sterile plant, so as to obtain a second rice plant carrying an exogenous gene, wherein the second rice plant can produce fertile female gametes, and therefore can perform self-fertilization, obtaining seeds carrying the exogenous gene and seeds not carrying the exogenous gene, each accounting for 50%. The seeds carrying the exogenous gene can be used as a rice female sterility maintenance line, so that the female sterile lines and maintenance lines can be continuously produced conveniently by self-crossing; and furthermore, the plant not carrying the exogenous gene (female sterile) can be used as the male parent of hybridization parents and provides pollens for the male sterile line. Thus, rice hybridization can be effectively achieved.

In the fourth aspect of the present invention, the present invention discloses a method for recovering the fertility of a rice female sterile plant. According to embodiments of the present invention, the method comprises introducing the above construct into a rice homozygous recessive female sterile plant.

In the fifth aspect of the present invention, the present invention discloses a method for making rice seeds. According to embodiments of the present invention, the method comprises the steps of: introducing the above construct into a rice plant, and subjecting the rice plant to self-fertilization to obtain seeds containing the construct as described above.

In the sixth aspect of the present invention, the present invention also provides a rice female sterile mutant osfms2. Compared with the wild-type plant, the mutant plant is normal in growth and development, and blooms in the same period. There is no difference from the wild-type plant in size, morphology, the opening size, and the opening time of the lemma and palea. The mutant has the anthers consistent with those of the wild-type in color, as yellow, the anthers can normally open, with normal pollen dispersal, and the staining assay on the pollen of the mutant using an I2-KI solution shows that the pollens in the mutant and the wild-type plants are stained normally. The appearances of female organs (comprising ovary, style and stigma) in the mutant and the wild-type are not obviously different. The gene clone analysis of the mutant and the genomic sequence alignment with the wild-type show that the allelic gene LOC_Os12g10540 in chromosome 12 of the mutant is mutated. In the wild-type Huang Huazhan, the full length of the encoding region of the gene OsFMS2 is 813 bp, the nucleotide sequence thereof is shown in SEQ ID NO: 1, and the amino acid sequence encoded thereby is as shown in SEQ ID NO: 2 containing 270 amino acids in total. However, in the female sterile mutant, the base at position 52 in the encoding region of the gene OsFMS2 is mutated from C to T, resulting in the mutation from CAG to a stop codon TAG, and leading to the early termination of the gene. The particular nucleotide sequence of mutated OsFMS2 is shown as SEQ ID NO: 5. In Nipponbare, the nucleotide sequence of the OsFMS2 is shown as SEQ ID NO: 3, and the amino acid sequence thereof is shown as SEQ ID NO: 4.

The additional aspects and advantages of the present invention will be provided partly in the following description, and some of them will become apparent from the following description, or understood via practice of the present invention.

PARTICULAR EMBODIMENTS

The following methods used in the embodiments below are all conventional methods, unless specially noted, and the primers used were all synthesized by Shanghai Invitrogen Biotechnology Incorporation, sequencing was completed by Beijing Sunbiotech Co., Ltd., PCR kits and endonucleases for the plasmids construction were purchased from Takara Biotechnology Co., Ltd., the pEASY-Blunt-simple cloning kit was purchased from Beijing TransGen Biotech, Inc., T4 DNA ligase was purchased from NEB Inc., and all the methods were performed according to the methods provided by the kits. The vector pCAMBIA2300 is from CAMBIA Inc.

Figure 17:
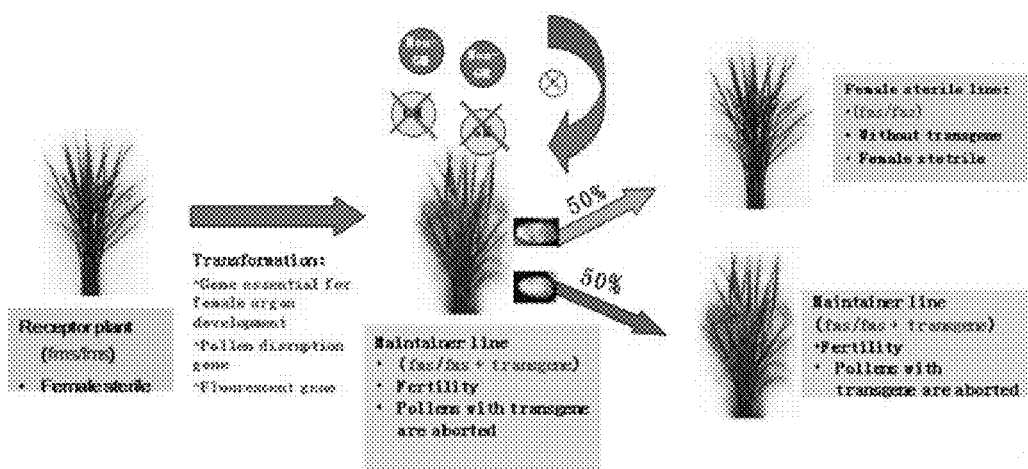
FIG. 17 is a flowchart of the method for propagating the female sterile line.

Embodiment 1. Propagation of Female Sterile Lines and Hybrid Seed Production Techniques The core concept of the technique is: a recessive nuclear female sterile mutant is used as a transformation receptor material, the sterile mutant is transformed with 3 target genes closely linked, wherein the female fertility gene can recover the female fertility of the transformation receptor, the pollen inactivation gene can inactivate the pollen containing the exogenous gene, i.e. lose the insemination capability, and the screening gene can be used for sorting the transgenic seeds and the non-transgenic seeds, wherein the sorted non-transgenic seeds are used as a female sterile line and transgenic seeds are used as a maintenance line. The female sterile line and maintenance line can thus be propagated by self-crossing and seed production of the maintenance line. During hybrid seed production, the female sterile line can pollinate the male sterile line to generate hybrid seeds, and the female sterile line itself cannot produce seeds, and cannot produce seeds by self-crossing to affect the purity of hybrid seeds, and thus needs not be removed after pollination. Therefore, the female sterile line and the male sterile line can be subjected to mixed sowing in production, to improve the cross pollination efficiency (i.e. hybrid species seed production efficiency) in natural conditions and reduce artificial pollination; the male parent plant needs not be removed after pollination, thereby reducing the labor cost during seed production and facilitating mechanized seed production. The propagation method of the female sterile line is shown as in FIG. 17, and the female sterile line and the male sterile line can be subjected to mixed sowing for hybrid seed production.

Embodiment 2. The Application of Rice Female Sterile Mutants and Genes in Breeding The rice female sterile mutant material and the female fertility gene which after been mutated will result in female sterility in a plant can be used in a new generation of hybridization breeding technique, and the core concept of the technique is: a recessive nuclear female sterile mutant is used as a transformation receptor material, the sterile mutant is transformed with 3 target genes closely linked, wherein the fertility gene can recover the fertility of the transformation receptor, the pollen inactivation gene can inactivate the pollen containing the exogenous gene, i.e. lose the insemination capability, and the screening gene can be used for sorting the transgenic seeds and the non-transgenic seeds, wherein the sorted non-transgenic seeds are used as a female sterile line and transgenic seeds are used as a maintenance line. The female sterile line and maintenance line can thus be propagated by self-crossing and seed production of the maintenance line. During hybrid seed production, the female sterile line can pollinate the male sterile line to generate hybrid seeds, and the female sterile line itself cannot produce seeds, and cannot produce seeds by self-crossing to affect the purity of hybrid seeds, and thus needs not be removed after pollination. Therefore, the male and the female sterile lines can be subjected to mixed sowing in production, to improve the cross pollination efficiency (i.e. hybrid species seed production efficiency) in natural conditions and reduce artificial pollination; the male parent plant needs not be removed after pollination, thereby reducing the labor cost during seed production and facilitating mechanized seed production.

Embodiment 3. The Screening of Rice Female Sterile Mutants (Osfms2)

The mutant is obtained by EMS mutagenesis of an indica rice variety, Huang Huazhan seeds (M0) with the EMS mutagenesis concentration of 0.7% and mutagenesis time of 20 hours, and the plants from the M0 generation seeds are harvested in mixtures after seed-setting to obtain a mutant pool (M1). The plants from M1 generation seeds are used for screening at the seed maturing stage to obtain sterile plants. Rice stubbles of the sterile plants are cut to regenerate, and the regenerated plants at the reproductive stage are tested for the pollen development and staining reaction using I2-KI staining. One mutant appears to be pollen fertile; however, the self-crossing of the plant results in complete sterility. The mutant is used as the female parent, still sterile with pollination of wild-type pollens, and the mutant is used as the male parent to perform pollination on a wild-type plant, resulting in seeds, which indicates that sterility is caused by female sterility and can be stably transmitted genetically. The mutant is judged to be a female sterile mutant, and is named as osfms2.

Embodiment 4. The Genetic Analysis of Rice Female Sterile Mutants (Osfms2)

The osfms2 female mutant sterile plant is used as a male parent and hybridized with the wild-type Huang Zhanhua, 36 F1 materials from hybridization all show fertility. Then the F1 generation plants are subjected to self-crossing and seeds are harvested in individual plants; in the 247 planted F2 generation plants, 65 plants show female sterility, 182 plants show a complete fertile phenotype, and the separation ratio of the sterile and fertile plants is close to 1:3, which indicates that the mutation is controlled by a recessive nuclear gene.

Embodiment 5. The Stability Analysis of Fertility of Rice Female Sterile Mutants (Osfms2)

In order to test whether the osfms2 mutant fertility is affected by conditions such as ambient lighting and temperature, F2 generation plants produced by self-crossing the F1 generation generated by hybridization of the sterile plant and the wild-type Huang Huazhan are planted in Shenzhen, Sanya, Hunan and Beijing; and the plant fertility and phenotypic separation ratio are further checked. In all locations, a separation ratio of 1:3 is shown between the sterile plants and the fertile plants (table 1), the sterile plants regenerated by cutting off the rice stubbles still represent as completely sterile, which indicates that the sterility phenotype of the mutant is not affected by environmental factors such as geographical latitudes, environments and seasons.

TABLE 1

Separation ratio of F2 generation produced by hybridization of rice female sterile mutants (osfms2) and wild type

| | Fertile plant number | Sterile plant number | $\chi^2$ (3:1) |
|---|---|---|---|
| Shenzhen | 107 | 37 | 0.037 |
| Sanya | 127 | 40 | 0.098 |
| Hunan | 98 | 29 | 0.318 |
| Beijing | 147 | 51 | 0.061 |

Embodiment 6. The Reproductive Organ Phenotype Analysis of Rice Female Sterile Mutants (Osfms2)

Figure 2:
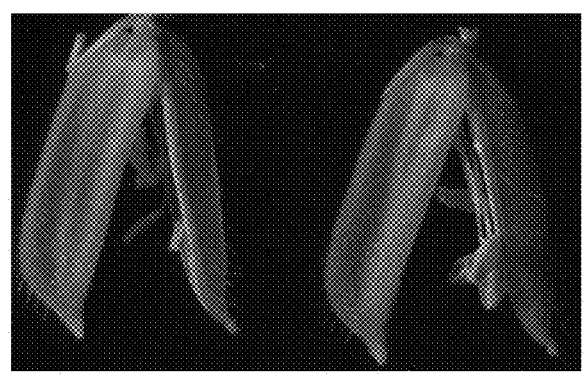
FIG. 2 shows floral morphologies of the osfms2 mutant and wild-type Huang Huazhan.
Figure 3:
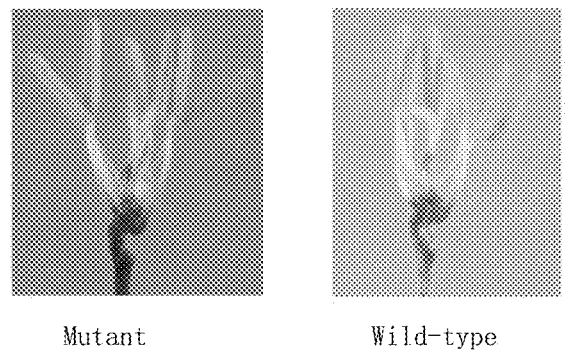
FIG. 3 shows anther morphologies of the osfms2 mutant and wild-type Huang Huazhan.
Figure 4:
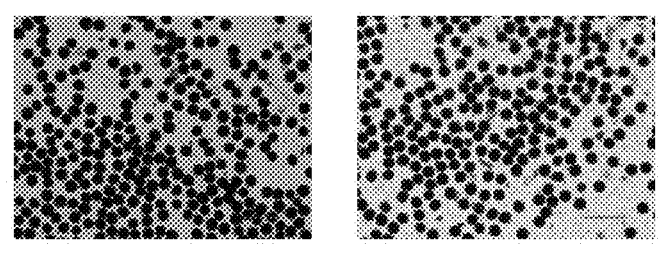
FIG. 4 shows pollen $I_2$-KI staining analysis of the osfms2 mutant and wild-type Huang Huazhan.
Figure 5:
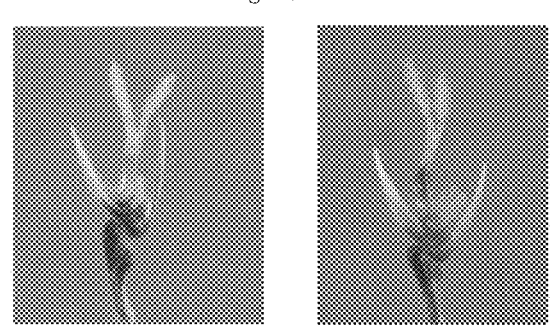
FIG. 5 shows a female organ morphology comparison of the osfms2 mutant and wild-type Huang Huazhan.

Compared with the wild-type plant, the mutant plant is normal in growth and development (FIG. 1), and blooms in the same period. There is no difference from the wild-type plant in size, morphology, the opening size, and the opening time of the lemma and palea (FIG. 2). The mutant has the anthers consistent with those of the wild-type in color, as yellow (FIG. 3), the anthers can normally open, with normal pollen dispersal, and the assay result of the staining on the pollen of the mutant using an $I_2$-KI solution is shown as in FIG. 4 that the pollens in the mutant and the wild-type plants are stained normally. The appearances of female organs (comprising ovary, style and stigma) in the mutant and the wild-type are not obviously different (FIG. 5).

Embodiment 7. The Cloning of Rice Female Sterile Mutant (Osfms2) Gene

The mutant gene cloning is performed using a MutMap method, i.e., a method of hybridizing the mutant with the original wild-type parent to construct F2 population and mapping genes by re-sequencing. The sterile plant as the male parent is hybridized with the wild-type Huang Huazhan to obtain F1, F1 is planted, F2 seeds are collected from a single plant and planted in individual lines, 30 F2 generation sterile plants are chosen from F2 line population with the separation ratio of 3:1, leaves are collected to extract genomic DNA, the DNAs are mixed in equal amounts and used for high throughout genomic sequencing, and 21 Gb genomic sequence data (PE101) are obtained in total, which are equal to 50× rice genomes.

After obtaining raw reads of F2 generation sterile plants, poor-quality reads (containing N≥5) are filtered, then SOAP2 is used for aligning the reads to Nipponbare reference genome, with an alignment rate of 74.87%, covering 88% of the whole genome. After alignment, soapsnp is used for finding SNPs existed between the sterile plant and the reference genome. Likewise, after aligning the re-sequencing data of the wild-type Huang Huazhan to Nipponbare reference genome and finding SNPs between the two, relatively reliable genotypes of the wild type Huang Huazhan at each SNP site can be obtained by calculating the frequencies of main genotypes at each SNP site of the wild-type Huang Huazhan and choosing cutoff ≥0.8 (covering depth ≥5). Subsequently, for all SNP sites between the sterile plant and the wild-type Huang Huazhan, main genotype frequencies and Euclidean distance (ED value) at these sites of the sterile plant are calculated, the region having a frequency of ≥0.8 and a higher ED value is taken as one which is possibly associated with the mutant trait; by inquiring the annotation information of the Nipponbare reference genome, SNP sites, which are located in vicinity of UTR (upstream 2.5 kbp from the gene as 5'-UTR, downstream 1.5 kbp as 3'-UTR), exon or splicing sites and can affect the function of the related gene, are selected as candidate mutant sites which might be associated with the mutant trait, and the related gene is taken as a candidate mutant gene.

The comparison with the genomic sequence of the wild-type Huang Huazhan shows that the mutant gene is the allelic gene LOC_Os12g10540 in chromosome 12. In the wild-type Huang Huazhan, the full length of the encoding region of the gene OsFMS2 is 813 bp, the nucleotide sequence thereof is shown as SEQ ID NO: 1, and the protein encoded thereby contains 270 amino acids whose amino acid sequence is shown as SEQ ID NO: 2. In the sterile mutant, the base at position 52 in the gene encoding region is mutated from C to T, resulting in the corresponding codon being mutated from CAG to a stop codon TAG, resulting in early termination of the gene (FIG. 6), the nucleotide sequence after mutation is shown as SEQ ID NO: 5, and the alignment result between the mutated nucleotide sequence and the wild-type sequence is shown in FIG. 6, wherein the base underlined is the base at the mutation site.

The verification is performed using SNP (Single Nucleotide Polymorphism) analysis strategy HRM (High Resolution Melt) for analyzing 280 F2 plants in total, which further verified that all the female sterile mutant plants carry homozygous mutation sites and the fertile plants carry homozygous wild-type or heterozygous sites. The progenies produced by self-crossing the plants in which the sites are homozygous wild-types are all fertile, and the progenies produced by self-crossing the plants in which the sites are heterozygous show a ratio of sterility:fertility being 68:212, meeting the separation ratio of 1:3.

Nucleotide sequence polymorphism exists in the encoding region of the gene OsFMS2 between japonica rice Nipponbare and the wild-type Huang Huazhan, the nucleotide sequence alignment result therebetween is shown in FIG. 7, and it can be seen from the figure that there are 5 different bases in total; and the alignment result of the amino acid sequence of the gene is shown in FIG. 8. The base differences at positions 81, 643 and 765 do not cause changes of amino acids, while the base at position 415 in Nipponbare is T and that in Huang Huazhan is G, accordingly, the amino acid at this site in Nipponbare is serine and that in Huang Huazhan is alanine; the base at position 781 in Nipponbare is G and that in Huang Huazhan is A, accordingly, the amino acid at this site in Nipponbare is alanine and that in Huang Huazhan is threonine; further analysis shows that the gene does not show polymorphism between indica type rice variety 9311 and the wild-type Huang Huazhan. In Nipponbare, the encoding region sequence of the gene OsFMS2 is shown as SEQ ID NO: 3, and the amino acid sequence encoded thereby is shown as SEQ ID NO: 4.

Embodiment 8. Hybridization Assay of Osfms2 Mutant Plants with Other Rice

Huang Huazhan osfms2 mutant plants can be hybridized with common cultivars (comprising sterile lines) in production to produce fertile seeds. The hybrid seeds produced in some combinations show prominent heterosis, indicating that the Huang Huazhan mutants have certain application value in hybridization breeding and can be used as parent materials for breeding restoring lines.

Embodiment 9. The Application of OsFMS2 Gene and the Mutant Thereof in Breeding

According to the principle in Embodiment 1, the inventor constructs the expression plasmid pFMS2 by using the rice OsFMS2 gene. Before constructing a plant expression plasmid of rice, the inventor firstly perform individual rice transformation with three expression cassettes of PA, OsFMS2 and RFP in the expression vector respectively, and further performs verification on the function of each of the expression cassettes. The results indicate that the individual rice transformation with each of the expression cassettes works well and achieves the expected design effects.

Furthermore, the inventor constructs the following rice expression vector: the pFMS2 vector shown as in FIG. 9 is constructed by assembling each element of expression frames of PA, OsFMS2 and RFP, wherein the vector contains 3 expression frames. The three expression frames respectively are a female fertility gene expression frame in which both the promoter and the terminator are corresponding endogenous regulatory sequences of the fertility gene OsFMS2, a pollen lethal expression frame in which the pollen lethal gene is PA, the promoter is PG47 and the terminator is IN2-1, wherein there is a leading peptide sequence ZM-BT1 before the PA gene for targeting the PA protein to an amyloplast; and a screening gene expression frame in which the screening gene is RFP gene, the promoter is Ltp2 and the terminator is PinII, wherein there is a 35S enhancer sequence before the promoter Ltp2.

Furthermore, the inventor constructs the pFMS2 plasmid shown as in FIG. 9 by assembling the following DNA elements:
1) the vector pCAMBIA2300 as a basis;
2) RFP gene expression cassette: the open reading frame of the RFP gene (SEQ ID NO: 6) is linked between the promoter LTP2 (SEQ ID NO: 7) and the terminator PINII (SEQ ID NO: 9), and a 35S enhancer sequence (SEQ ID NO: 8) is further linked at the upstream of the promoter LTP2, thereby recombining the RFP gene expression cassette (LTP2: RFP: PINII);
3) OsFMS2 gene expression cassette: the full-length nucleotide sequence of the target gene OsFMS2 and its promoter and terminator is shown as SEQ ID NO: 10, wherein the promoter sequence of the OsFMS2 gene is shown as SEQ ID NO: 11, the terminator thereof is shown as SEQ ID NO: 12, and the amino acid sequence of the protein encoded by the nucleotide sequence is shown as SEQ ID NO: 2;
and 4) PA gene expression cassette: PG47, ZM-BT1, PA and IN2-1, wherein the open reading frame of the target gene PA (the nucleotide sequence thereof is shown as SEQ ID NO: 13) is linked at the downstream of the promoter PG47 (the nucleotide sequence thereof is shown as SEQ ID NO: 14) and the transit peptide ZM-BT1 (the nucleotide sequence thereof is shown as SEQ ID NO: 15) and at the upstream of the terminator IN2-1 (the nucleotide sequence thereof is shown as SEQ ID NO: 16).

Rice Transformation

Electroporation is used for transforming the plasmid pFMS2 into an agrobacterium, Ag10 strain, and the osfms2 rice having OsFMS2 homozygous recessive mutation is genetically transformed using an agrobacterium-mediated method, obtaining 26 single copy transgenic plant materials. The specific transformation receptor material cultivar is rice Huang Huazhan.

Pollen Fertility Detection of a Transgenic Rice Plant

It is found from the analysis on the above obtained 26 single copy transgenic rice (having homozygous recessive mutation at OsFMS2 site) plants that there is no apparent morphological difference between the transgenic plants and the non-transgenic control plants, but the pollen fertility is obviously different. The pollen stain-ability is detected for the transgenic plant materials resulting from the transformation with pFMS2 construct, meanwhile the pollen stain-ability for the wild-type rice is detected. The method used is: in rice flowering stage, a plurality of individual plants are randomly selected from the transgenic rice plants and the wild-type control plants respectively, one flower is taken for each plant, one anther is taken for each flower, placed in the middle of a glass slide, one drop of 1% I2-KI solution is dripped, the pollens are released with tweezers and a dissecting needle followed by covering a cover slip, and the stainable pollen number and the pollen total number are observed and counted under a microscope, wherein the pollens which can be stained as deep blue are fertile pollens and those which cannot be stained are abortive pollens. Pollen stain-ability of a transgenic rice plant is analyzed. The result shows that the stainable pollens in the wild-type control plants account for 98%400%; in the plurality of randomly selected transgenic plants, the ratio between normal pollens (stainable) and abortive pollens (not stainable) is close to 1:1, indicating the constructed transgenic lines can produce equal amounts of pollens carrying an exogenous gene and pollens not carrying the exogenous gene, i.e. the construct pFMS2 inactivates 50% of the pollens of the transgenic lines. The result indicates that the plasmid construct provided herein can achieve expected pollen inactivation function.

Separation Analysis on Fluorescent Seeds and Non-Fluorescent Seeds of the Transgenic Rice Plants Fluorescent separation ratio of T1 generation seeds produced by the 26 single copy transgenic rice plants (having homozygous recessive mutation at OsFMS2 site) resulting from the above embodiment is investigated, and the result indicates that all the seeds show a separation ratio of 1:1 (FIG. 10), i.e., the fluorescent seeds carrying the exogenous gene and non-fluorescent seeds not carrying the exogenous gene show a separation of 1:1, indicating that each element of the plasmid provided herein performs well as a whole and expected purposes are achieved.

Embodiment 9. The Application of OsFMS1 Gene and the Mutant Thereof in Breeding

Figure 11:
FIG. 11 shows phenotypes of osfms1 mutant and the wild-type plant at the heading stage, wherein the left panel is the wild-type plant, the right panel is the mutant with the leaves hanging upside down.
Figure 12:
FIG. 12 shows phenotypes of panicles in osfms1 mutant and the wild-type plant, wherein the left panel is the wild-type, the middle panel is heterozygote, and the right panel is the homozygous mutant.

Besides the above-mentioned OsFMS2 gene, another gene OsFMS1 (LOC_Os03g11600) controlling the rice female fertility has also been cloned. The stamens of the osfms1 mutant are totally normal in growth and development, and the pistil appearance is not remarkably different from the wild-type except slightly smaller than the wild-type, possibly due to the abnormal proliferation in integument development according to further cytological observation. The mutant is completely sterile by self-crossing; using the mutant as the female parent, still sterile with pollination of wild-type pollens; and the sterility phenotype is not affected by geographical latitudes, environments and seasons, indicating the sterility is caused by female sterility and can be stably transmitted genetically. Starting from the later period of tillering, upper leaves (comprising boot leaves) and main veins of the mutant is under development or mostly degenerated, resulting in the leaves hanging upside down (FIG. 11), the panicles of the recessive mutant materials are completely sterile (FIG. 12), furthermore the phenotype of hanging upside down of the leaves are completely linked with the female sterility phenotype.

The mutant as a male parent is hybridized with the wild-type, obtaining 20 F1 generation plants which are all fertile, the F1 generation plants are subjected to self-crossing and seeds are harvested in individual plants, and in 1200 planted F2 generation plants, 312 plants show female sterility, 888 plants show a complete fertile phenotype, and the separation ratio of the sterile and fertile plants is close to 1:3, which indicates that the mutation is controlled by a recessive nuclear gene. The gene clone analysis of the mutant and the sequence alignment with the wild-type genome show that the allelic gene LOC_Os03g11600 in chromosome 3 of the mutant is mutated. The full length of the encoding region of the gene is 591 bp, the nucleotide sequence thereof is shown in SEQ ID NO:17, and the amino acid sequence encoded thereby is as shown in SEQ ID NO: 18 containing 196 amino acids in total. However, in the female sterile mutant, the base at position 83 in the gene encoding region is mutated from T to C, resulting in the corresponding codon being mutated from GTC to GCC, resulting in the encoded amino acid being mutated from valine to alanine, and the nucleotide sequence of the mutated gene is shown as in SEQ ID NO: 19. The alignment result between the wild-type nucleotide sequence and the mutant nucleotide sequence of the gene OsFMSJ is shown in FIG. 13, and the alignment result of the amino acid sequences is shown as in FIG. 14.

The female sterile mutant shows complete female sterility, stable male fertility, and also recessive inheritance, and the female sterility property can be applied to hybrid rice seed production by hybridization breeding so as to achieve mechanized production preparation of hybrid rice seeds. Meanwhile, the mutant shows female sterility, at the same time, the middle-upper parts of the leaves are curved and hang upside down at leaf rings, and such a recessive inheritable trait of the upper layer of leaves being naturally curved down is transmitted to a hybrid rice parent would reduce barriers in seed production and breeding, improve the seed production yield and decrease the labor cost. Therefore, the gene likewise has an application prospect in hybrid rice.

Like pFMS2, the inventor use the rice OsFMSJ gene to construct an expression plasmid, pFMS1, the pFMS1 expression plasmid also contains three expressing cassettes of OsFMSJ gene, PA and RFP, and the plasmid pFMS1 as shown in FIG. 15 is constructed by assembling each element in expressing frames of PA, OsFMS1 and RFP, wherein the plasmid contains 3 expression frames.

1) The vector pCAMBIA2300 as a basis;
2) RFP gene expression cassette: the open reading frame of the RFP gene (SEQ ID NO: 6) is linked between the promoter LTP2 (SEQ ID NO: 7) and the terminator PINII (SEQ ID NO: 9), wherein a 35s enhancer sequence (SEQ ID NO: 8) is further linked at the upstream of the promoter LTP2, thereby recombining the RFP gene expression cassette (LTP2: RFP: PINII);
3) OsFMSJ gene expression cassette: the full-length nucleotide sequence of the target gene OsFMSJ and its promoter and terminator is shown as SEQ ID NO: 20, wherein the promoter sequence of the OsFMSJ gene is shown as SEQ ID NO: 21, the terminator thereof is shown as SEQ ID NO: 22, and the amino acid sequence of the protein encoded by the nucleotide sequence is shown as SEQ ID NO: 18; and,
4) PA gene expression cassette: PG47, ZM-BT1, PA and IN2-1, wherein the open reading frame of the target gene PA (the nucleotide sequence thereof is shown as SEQ ID NO: 13) is linked at the downstream of the promoter PG47 (the nucleotide sequence thereof is shown as SEQ ID NO: 14) and the transit peptide ZM-BT1 (the nucleotide sequence thereof is shown as SEQ ID NO: 15) and at the upstream of the terminator IN2-1 (the nucleotide sequence thereof is shown as SEQ ID NO: 16).

Rice Transformation

Electroporation is used for transforming the plasmid pFMS1 into an agrobacterium, Ag10 strain, and the homozygous recessive osfms1 rice is genetically transformed using an agrobacterium-mediated method, obtaining 19 single copy transgenic plant materials.

Pollen Fertility Detection of a Transgenic Rice Plant

It is found from the analysis on the above obtained 19 single copy transgenic rice (having homozygous recessive mutation at OsFMS1 site) plants that there is no apparent morphological difference between the transgenic plants and the non-transgenic control plants, and the pollen fertility is obviously different. The pollen stain-ability is detected for the transgenic plant materials resulting from the transformation with pFMS1 construct, meanwhile the pollen stain-ability for the wild-type rice is detected. The method used is: in rice flowering stage, a plurality of individual plants are randomly selected from the transgenic rice plants and the wild-type control plants respectively, one flower is taken for each plant, one anther is taken for each flower, placed in the middle of a glass slide, one drop of 1% I2-KI solution is dripped, the pollens are released with tweezers and a dissecting needle followed by covering a cover slip, and the stainable pollen number and the pollen total number are observed and counted under a microscope, wherein the pollens which can be stained as deep blue are fertile pollens and those which cannot be stained are abortive pollens. Pollen stain-ability of a transgenic rice plant is analyzed. The result shows that the stainable pollens in the wild-type control plants account for 98%400%; in the plurality of randomly selected transgenic plants, the ratio between normal pollens (stainable) and abortive pollens (not stainable) is close to 1:1, indicating the constructed transgenic lines can produce equal amounts of pollens carrying an exogenous gene and pollens not carrying the exogenous gene, i.e. the construct pFMS1 inactivates 50% of the pollens of the transgenic lines. The result indicates that the plasmid provided herein can achieve expected pollen inactivation function.

Figure 16:
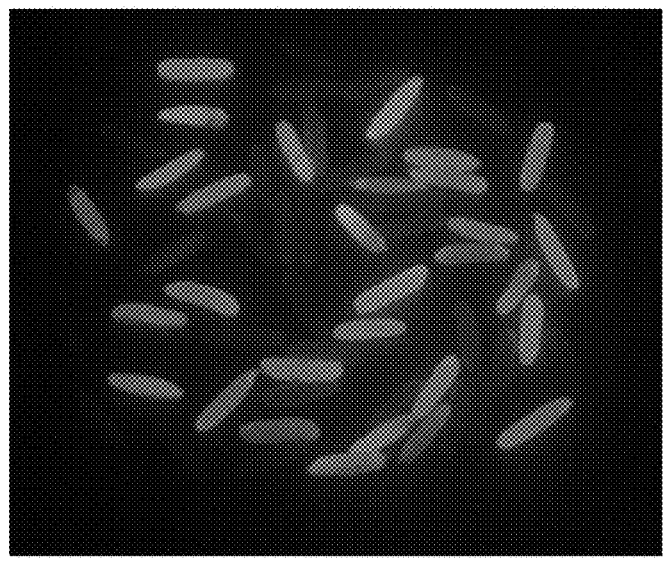
FIG. 16 shows that fluorescent seeds carrying the exogenous construct in FIG. 15 and non-fluorescent seeds not carrying the exogenous construct show 1:1 separation ratio.

Separation Analysis on Fluorescent Seeds and Non-Fluorescent Seeds of the Transgenic Rice Plants Fluorescent separation ratio of T1 generation seeds produced by the 19 single copy transgenic rice plants (having homozygous recessive mutation at OsFMS1 site) resulting from the above embodiment is investigated, and the result indicates that all the seeds show a separation ratio of 1:1 (FIG. 16), i.e., the fluorescent seeds carrying the exogenous gene and non-fluorescent seeds not carrying the exogenous gene represent a separation of 1:1, indicating that each element of the plasmid provided herein performs well as a whole and expected purposes are achieved.

Embodiment 10. Other Rice Female Fertility Gene

Aside from the above two cloned rice female fertility genes, for other genes regulating female organ development, female sterile mutants can be obtained by technical strategy of mutation screening or site-specific mutagenesis methods such as CRISPR/Cas, and can thus be applied to rice hybrid seed production by the methods of the present patent.

For example, the inventor also obtains another mutant plant of OsFMS2 through mutagenesis screening, wherein a splicing recognition site in an intron between the 3rd and 4th exons of OsFMS2, "GT-AG" is mutated to "AT-AG", and the mutated genomic DNA sequence is SEQ ID NO: 23, thereby a female sterile mutant plant is also obtained and can be applied to rice hybrid seed production by the methods of the present patent.

The invention claimed is:

1. A DNA construct, comprising:
   i) a first nucleotide sequence selected from the group consisting of OsFMS2 gene and OsFMS 1 gene;
   ii) a second nucleotide sequence selected from a group consisting of maize α-amylase gene, auxin gene, rot B gene, cytotoxin gene, diphtherin gene, DAM methylase gene, and PA gene;
   iii) a third nucleotide sequence selected from the group consisting of chloromycetin resistance gene, hygromycin resistance gene, streptomycin resistance gene, miramycin resistance gene, sulfonamide resistance gene, glyphosate resistance gene, glufosinate resistance gene, red fluorescence protein gene, cyan fluorescent protein gene, yellow fluorescent protein gene, luciferase gene, green fluorescent protein gene, an anthocyanin p1 gene, and blue fluorescent protein gene, and
   at least one regulatory nucleotide sequence that allows expression of the first, the second and the third nucleotide sequences in a plant,
   wherein the OsFMS2 gene has a nucleotide sequence selected from the group consisting of SEQ ID NOS:1 and 2, and
   wherein the OsFMS1 gene has a nucleotide sequence selected from the group consisting of SEQ ID NOS:17 and 18.

2. The construct of claim 1, wherein the at least one regulatory nucleotide sequence comprises a fourth nucleotide sequence, wherein the fourth nucleotide sequence is operably linked to the first nucleotide sequence and drives the first nucleotide sequence to express in a female organ of the plant.

3. The construct of claim 1, wherein the at least one regulatory nucleotide sequence comprises a fifth nucleotide sequence, wherein the fifth nucleotide sequence is operably linked to the second nucleotide sequence and drives the second nucleotide sequence to express in male gametes of the plant.

4. The construct of claim 3, wherein the fifth nucleotide sequence is selected from the group consisting of the regulatory regions of polygalacturonase 47 gene, Zm13 gene, pectin methylesterase gene, calmodulin binding protein gene, actin depolymerizing factor gene, prolfilin gene and sulfated pentapeptide phytosulphokine gene.

5. The construct of claim 1, wherein the third nucleotide sequence is operably linked to a sixth nucleotide sequence, wherein the sixth nucleotide sequence is a promoter that drives the third nucleotide sequence to express specifically in a seed or endosperm of the plant.

6. The construct of claim 5, wherein the sixth nucleotide sequence comprises a END2 promoter or a LTP2 promoter.

7. The construct of claim 1, wherein the first nucleotide sequence comprises OsFMS2 gene with a nucleotide sequence selected from the group consisting of SEQ ID NOS:1 and 2.

8. A DNA construct, comprising:
   i) a first nucleotide sequence selected from the group consisting of OsFMS2 gene and OsFMS 1 gene;
   ii) a second nucleotide sequence selected from a group consisting of maize α-amylase gene, auxin gene, rot B gene, cytotoxin gene, diphtherin gene, DAM methylase gene, and PA gene;

iii) a third nucleotide sequence selected from the group consisting of chloromycetin resistance gene, hygromycin resistance gene, streptomycin resistance gene, miramycin resistance gene, sulfonamide resistance gene, glyphosate resistance gene, glufosinate resistance gene, red fluorescence protein gene, cyan fluorescent protein gene, yellow fluorescent protein gene, luciferase gene, green fluorescent protein gene, an anthocyanin p1 gene, and blue fluorescent protein gene;

a fourth nucleotide sequence, wherein the fourth nucleotide sequence is operably linked to the first nucleotide sequence and drives the first nucleotide sequence to express in a female organ of the plant;

a fifth nucleotide sequence, wherein the fifth nucleotide sequence is operably linked to the second nucleotide sequence and drives the second nucleotide sequence to express in male gametes of the plant; and a sixth nucleotide sequence, wherein the sixth nucleotide sequence is a promoter that drives the third nucleotide sequence to express specifically in seeds or endosperm, wherein the OsFMS2 gene has a nucleotide sequence selected from the group consisting of SEQ ID NOS:1 and 2, and wherein the OsFMS1 gene has a nucleotide sequence selected from the group consisting of SEQ ID NOS:17 and 18.

9. A method for propagating a homozygous recessive nuclear female sterile line, comprising:
(a) providing a first plant, wherein a nuclear gene regulating the female organ development of the first plant has a homozygous recessive mutation, and the first plant shows female sterility;
(b) introducing the DNA construct of claim 1 to the first plant to form a second plant; and
(c) self-pollinating the second plant.

10. The method of claim 9, wherein the first nucleotide sequence comprises OsFMS2 gene with a nucleotide sequence selected from the group consisting of SEQ ID NOS:1 and 2.

11. The method of claim 9, wherein the first nucleotide sequence is operably linked to a fourth nucleotide sequence, wherein the fourth nucleotide sequence drives the first nucleotide sequence to express in female organ.

12. The method of claim 9, wherein the second nucleotide sequence is operably linked to a fifth nucleotide sequence, wherein the fifth nucleotide sequence drives the second nucleotide sequence to express in male gametes.

13. The method of claim 12, wherein the fifth nucleotide sequence is selected from the group consisting of regulatory regions of polygalacturonase 47 gene, Zm13 gene, pectin methylesterase gene, calmodulin binding protein gene, actin depolymerizing factor gene, prolfilin gene and sulfated pentapeptide phytosulphokine gene.

14. The method of claim 9, wherein the third nucleotide sequence is operably linked to a sixth nucleotide sequence, wherein the sixth nucleotide sequence is a promoter that drives the third nucleotide sequence to express specifically in a seed or endosperm.

15. The method of claim 14, wherein the sixth nucleotide sequence comprises a END2 promoter or a LTP2 promoter.

* * * * *